(12) United States Patent
Gerder et al.

(10) Patent No.: US 12,292,429 B2
(45) Date of Patent: May 6, 2025

(54) MONITORING SYSTEM

(71) Applicant: Dräger Safety AG & Co. KGaA, Lübeck (DE)

(72) Inventors: Henning Gerder, Lübeck (DE); Christoph Osterloh, Lübeck (DE)

(73) Assignee: Dräger Safety AG & Co. KGaA, Lübeck (DE)

( * ) Notice: Subject to any disclaimer, the term of this patent is extended or adjusted under 35 U.S.C. 154(b) by 735 days.

(21) Appl. No.: 17/355,751

(22) Filed: Jun. 23, 2021

(65) Prior Publication Data

US 2021/0405008 A1 Dec. 30, 2021

Related U.S. Application Data

(60) Provisional application No. 62/705,456, filed on Jun. 29, 2020.

(30) Foreign Application Priority Data

Jun. 29, 2020 (DE) ..................... 10 2020 117 040.8
May 4, 2021 (DE) ..................... 10 2021 111 431.4

(51) Int. Cl.
*G06Q 30/02* (2023.01)
*A62B 9/00* (2006.01)
(Continued)

(52) U.S. Cl.
CPC ......... *G01N 33/0063* (2013.01); *A62B 9/006* (2013.01); *G01N 33/0011* (2013.01); *A62B 7/14* (2013.01)

(58) Field of Classification Search
CPC ............ G01N 33/0063; G01N 33/0011; A62B 9/006; A62B 7/14; Y02A 50/20
See application file for complete search history.

(56) References Cited

U.S. PATENT DOCUMENTS 2,944,418 A 4/1956 Engelhardt
2,816,863 A 12/1957 Page
(Continued)

FOREIGN PATENT DOCUMENTS

DE 2155935 A1 6/1972
DE 3319186 A1 11/1984
(Continued)

OTHER PUBLICATIONS

University of Chicago, Measurement of Gas-Exchange, Freshwater Science vol. 37 No. 2 (Year: 2018).*
(Continued)

*Primary Examiner* — Breffni Baggot
(74) *Attorney, Agent, or Firm* — McGlew and Tuttle, P.C.

(57) ABSTRACT

A monitoring system (100) is provided for flight crew members (99), e.g., aviators, pilots, copilots or passengers, of airplanes or aircraft, e.g., airplanes or helicopters of the civil or military aviation, passenger planes in the scheduled or charter service, especially also ultrafast passenger planes. The monitoring system includes a sensor mechanism and a control unit configured to organize a procedure of a measurement-based monitoring of the gas composition of air, breathing air or breathing gases with the sensor mechanism in an airplane or aircraft, and to control or regulate the procedure. A measurement-based detection of gas concentrations is carried out with the sensor mechanism (60).

36 Claims, 11 Drawing Sheets

(51) Int. Cl.
*G01N 33/00* (2006.01)
*A62B 7/14* (2006.01)

(56) References Cited

U.S. PATENT DOCUMENTS

| | | | |
|---|---|---|---|
| 3,584,499 | A | 6/1971 | Hummel |
| 3,646,803 | A | 3/1972 | Meyer |
| 4,050,823 | A | 9/1977 | Frankenberger |
| 4,173,975 | A | 11/1979 | Delong et al. |
| 4,175,422 | A | 11/1979 | Owen |
| 4,667,157 | A | 5/1987 | Ciammaichella et al. |
| 4,683,426 | A | 7/1987 | Hummel |
| 4,808,921 | A | 2/1989 | Christensen |
| 4,851,088 | A | 7/1989 | Chandrasekhar et al. |
| 4,902,138 | A | 2/1990 | Goeldner et al. |
| 5,026,992 | A | 6/1991 | Wong |
| 5,067,492 | A | 11/1991 | Yelderman et al. |
| 5,095,900 | A | 3/1992 | Fertig et al. |
| 5,473,304 | A | 12/1995 | Friese et al. |
| 5,696,379 | A | 12/1997 | Stock |
| 5,739,535 | A | 4/1998 | Koch et al. |
| 5,789,660 | A | 8/1998 | Kofoed et al. |
| 5,902,556 | A | 5/1999 | Van De Vyver et al. |
| 5,942,755 | A | 8/1999 | Dreyer |
| 5,958,200 | A | 9/1999 | Kessel |
| 6,095,986 | A | 8/2000 | Braig et al. |
| 6,274,879 | B1 | 8/2001 | Best-Timmann |
| 6,312,389 | B1 | 11/2001 | Kofoed et al. |
| 6,344,174 | B1 | 2/2002 | Miller et al. |
| 6,405,578 | B2 | 6/2002 | Chiba et al. |
| 6,430,987 | B1 | 8/2002 | Stark |
| 6,571,622 | B2 | 6/2003 | Koch |
| 6,616,896 | B2 | 9/2003 | Labuda et al. |
| 6,756,016 | B2 | 6/2004 | Miller et al. |
| 6,895,802 | B2 | 5/2005 | Stark et al. |
| 6,952,947 | B2 | 10/2005 | Steinert et al. |
| 6,954,702 | B2 | 10/2005 | Pierry et al. |
| 7,183,552 | B2 | 2/2007 | Russell |
| 7,264,647 | B2 | 9/2007 | Meckes et al. |
| 7,335,164 | B2 | 2/2008 | Mace et al. |
| 7,391,574 | B2 | 6/2008 | Fredriksson |
| 7,407,528 | B2 | 8/2008 | Rittner et al. |
| 7,432,508 | B2 | 10/2008 | Daniels et al. |
| 7,501,630 | B2 | 3/2009 | Russell |
| 7,606,668 | B2 | 10/2009 | Pierry et al. |
| 7,684,931 | B2 | 3/2010 | Pierry et al. |
| 7,705,991 | B2 | 4/2010 | Doering et al. |
| 7,875,244 | B2 | 1/2011 | Schlichte et al. |
| 7,897,109 | B2 | 3/2011 | Labuda et al. |
| 8,080,798 | B2 | 12/2011 | Russell |
| 8,210,175 | B2 | 7/2012 | Meckes et al. |
| 8,399,839 | B2 | 3/2013 | Huettmann et al. |
| 8,425,846 | B2 | 4/2013 | Takahashi et al. |
| 8,448,642 | B2 | 5/2013 | Tappehorn et al. |
| 8,496,795 | B2 | 7/2013 | Kuehn |
| 8,596,109 | B2 | 12/2013 | Stark et al. |
| D727,492 | S | 4/2015 | Scampoli |
| 9,089,721 | B1 | 7/2015 | Horstman et al. |
| 9,234,876 | B2 | 1/2016 | Le Neel et al. |
| 9,360,441 | B2 | 6/2016 | Heise et al. |
| 9,459,235 | B2 | 10/2016 | Soundarrajan et al. |
| 9,625,406 | B2 | 4/2017 | Zanella, Sr. |
| 9,818,937 | B2 | 11/2017 | Le Neel et al. |
| 9,867,563 | B2 | 1/2018 | Peake |
| 9,939,374 | B2 | 4/2018 | Buchtal et al. |
| 9,958,305 | B2 | 5/2018 | Nakano et al. |
| 10,561,863 | B1* | 2/2020 | Dashevsky ........... A61B 5/6803 |
| 10,786,693 | B1* | 9/2020 | Opperman ............. A62B 18/02 |
| 2002/0036266 | A1 | 3/2002 | Dreyer et al. |
| 2003/0194351 | A1 | 10/2003 | Tuomela |
| 2004/0203169 | A1 | 10/2004 | Dreyer et al. |
| 2004/0238746 | A1 | 12/2004 | Dreyet et al. |
| 2004/0245390 | A1 | 12/2004 | Meckes et al. |
| 2007/0181129 | A1 | 8/2007 | Mattinson et al. |
| 2008/0264418 | A1 | 10/2008 | Schermeier et al. |
| 2009/0301479 | A1 | 12/2009 | Pedarzini et al. |
| 2009/0320380 | A1* | 12/2009 | Chelf ................... A01G 9/1407 454/239 |
| 2010/0221148 | A1 | 9/2010 | Oie et al. |
| 2013/0167843 | A1 | 7/2013 | Kimm et al. |
| 2013/0306073 | A1 | 11/2013 | Fromage |
| 2016/0178412 | A1 | 6/2016 | Dittrich et al. |
| 2016/0253561 | A1 | 9/2016 | Foley et al. |
| 2016/0030340 | A1 | 10/2016 | Elliott et al. |
| 2018/0003354 | A1 | 1/2018 | Kastner-Jung et al. |
| 2018/0110957 | A1 | 4/2018 | Hansmann et al. |
| 2018/0014317 | A1 | 5/2018 | Hansmann et al. |
| 2018/0116555 | A1 | 5/2018 | Dreyer et al. |
| 2018/0120224 | A1 | 5/2018 | Dreyer et al. |
| 2018/0126194 | A1 | 5/2018 | Salin et al. |
| 2018/0133420 | A1 | 5/2018 | Hansmann et al. |
| 2018/0143170 | A1 | 5/2018 | Hansmann et al. |
| 2018/0143171 | A1 | 5/2018 | Hansmann et al. |
| 2018/0163712 | A1 | 6/2018 | Hansmann |
| 2018/0029075 | A1 | 10/2018 | Peake et al. |
| 2019/0105457 | A1 | 4/2019 | Baba et al. |
| 2019/0118008 | A1 | 4/2019 | Thompson et al. |
| 2019/0120821 | A1* | 4/2019 | Atsalakis ............... A61B 5/087 |
| 2019/0178827 | A1 | 6/2019 | Schlichte et al. |
| 2020/0061319 | A1* | 2/2020 | Hansmann .......... A61M 16/085 |
| 2022/0180075 | A1* | 6/2022 | Temkin .................. H04B 5/77 |
| 2022/0339470 | A1* | 10/2022 | Bowden ............ A61M 15/0001 |

FOREIGN PATENT DOCUMENTS

| | | |
|---|---|---|
| DE | 4020385 A1 | 1/1992 |
| DE | 19610912 A1 | 9/1997 |
| DE | 4020385 C2 | 11/1999 |
| DE | 19726453 C2 | 8/2000 |
| DE | 19912100 A1 | 10/2000 |
| DE | 102005007539 A1 | 8/2006 |
| DE | 102005026491 B4 | 5/2007 |
| DE | 102006030242 A1 | 6/2007 |
| DE | 102005026306 B4 | 7/2007 |
| DE | 102004048979 B4 | 12/2007 |
| DE | 102009010773 B4 | 7/2011 |
| DE | 102004062052 B4 | 12/2011 |
| DE | 102012022136 B4 | 1/2014 |
| DE | 102008056279 B4 | 2/2014 |
| DE | 102010047159 B4 | 3/2015 |
| DE | 102010037923 B4 | 8/2015 |
| DE | 202012013442 U1 | 1/2017 |
| DE | 102016013756 A1 | 5/2018 |
| DE | 102010014222 B4 | 3/2019 |
| DE | 102017009605 A1 | 4/2019 |
| DE | 102017009606 A1 | 6/2019 |
| DE | 102018004341 A1 | 12/2019 |
| DE | 10 2019 004 760 A1 | 2/2020 |
| EP | 0149619 A1 | 7/1985 |
| EP | 2148616 B1 | 1/2016 |
| EP | 3287173 A1 | 2/2018 |
| EP | 2788739 B1 | 9/2019 |
| GB | 2210980 A | 6/1989 |
| JP | H04138174 A | 5/1992 |
| JP | 2009297513 A | 12/2009 |
| JP | 2013059384 A | 4/2013 |
| JP | 2014522973 A | 9/2014 |
| JP | 2017503571 A | 2/2017 |
| NO | 2018033224 A1 | 2/2018 |
| WO | 16162287 A1 | 10/2016 |
| WO | 2018033225 A1 | 2/2018 |
| WO | 2019072606 A1 | 4/2019 |
| WO | 2019115571 A1 | 6/2019 |
| WO | 20109115 A1 | 6/2020 |

OTHER PUBLICATIONS

Dräger Safety AG & Co. KGAA (Hrsg.):Dräger-Röhrchen & CMS-Handbuch. 18. Ausgabe. Lübeck: Dräger Safety AG & Co. KGaA, März 2018. S. 73-406. URL: https://www.fischer-feuerschutz.de/_

(56) References Cited

OTHER PUBLICATIONS pdf/archiv/Draeger_Roehrchen_CMS_Handbuch_2018.pdf [abgerufen am May 4, 2024].

* cited by examiner

MONITORING SYSTEM

CROSS REFERENCE TO RELATED APPLICATIONS

This application claims the benefit of priority under 35 U.S.C. § 119 of German Application 10 2020 117 040.8, filed Jun. 29, 2020, U.S. Provisional Application 62/705, 456, filed Jun. 29, 2020, and German Application 10 2021 111 431.4, filed May 4, 2021, the entire contents of which are incorporated herein by reference.

TECHNICAL FIELD

The present invention pertains to a monitoring system for flight crew members or passengers of airplanes or aircraft. Airplanes or aircraft are defined as airplanes or helicopters of the civil or military aviation, e.g., passenger planes in scheduled or charter service as well as ultrafast airplanes close to the range or above the range of supersonic speed. In particular, flights with jet planes (jets) with supersonic speeds and/or at flight altitudes above 15,000 m above sea level represent high requirements on the flight crew members, especially on the pilots of jet planes, concerning the fitness to fly comprising physical and mental fitness, attention, ability to concentrate and alertness. In order for the physical and mental fitness and the alertness necessary for piloting the aircraft to be guaranteed at any time at high altitudes, during terrifically fast flight maneuvers or in flight positions, for example, curve flight, during nosedives, inverted flying at high speeds (>Mach 1) and with accelerations above or even several times the gravitational acceleration as well as also in-flight refueling, secured supply of the aviator with satisfactory breathing air that is harmless for health is also very essential in addition to a reliable equipment of the airplane. For example, systems which use—usually processed or air-conditioned and filtered—outside air from the environment as the source of the breathing gas, are used to supply aviators, pilots, copilots or passengers with breathing air or breathing gas, but systems in which additional oxygen is added to the breathing air or to the breathing gas are used as well. The oxygen may be carried along in the airplane here, for example, under high pressure (<200 bar) in compressed oxygen cylinders and its pressure can be reduced to a pressure suitable for breathing by means of suitable pressure-reducing devices or it may be generated for the consumption during the mission by a chemical oxygen generator, for example, from sodium chlorate, which is carried along, in a chemical process. It is often made possible for the aviator, pilot or copilot to activate the dispensing or supply of oxygen independently and/or to set or preset the quantity and/or a concentration of oxygen and/or a composition of the breathing gas independently. The breathing air/breathing gas supply may be ensured in this case directly from the air of the cabin or cockpit, but it is also possible to use a tube system with mouth/nose mask for the direct feed and/or removal of breathing air/breathing gas to the aviator, pilot or copilot. It is necessary in each case for the on-board equipment of the airplane or aircraft to supply the aviator, pilot or copilot during the mission with satisfactory breathing gas that is harmless for the health. This includes, on the one hand, that the qualitative and quantitative composition of the breathing gas, especially the percentages of oxygen and/or carbon dioxide, in the breathing gas be in a range that is harmless for health. In addition to such components as nitrogen and noble gases, oxygen ($O_2$) is present in the natural atmosphere at a percentage of 21 vol. %. The percentage of carbon dioxide ($CO_2$) is currently below 0.05 vol. % as a worldwide average in the natural atmosphere. According to recommendations of the U.S. Federal Aviation Administration (FAA), a carbon dioxide concentration of 30,000 ppm, corresponding to 3 vol. % $CO_2$, represents the highest allowable value for passengers in airplanes. The American Society of Heating, Refrigerating and Air-Conditioning Engineers (ASHRAE) recommends as the upper limit a carbon dioxide concentration of 1,000 ppm, corresponding to 0.1 vol. % of $CO_2$. Thus, a concentration above 21 vol. % is also desirable for the supply of breathing gas for aviators, pilots or copilots or passengers for the percentage of oxygen and an upper limit of 0.1 vol. % of $CO_2$ is desirable for the concentration of carbon dioxide during the mission at least according to the recommendations of the U.S. Federal Aviation Administration (FAA) and according to the recommendations of the American Society of Heating, Refrigerating and Air-Conditioning Engineers (ASHRAE). It is considered to be scientifically ascertained that concentrations of carbon dioxide above 1 vol. % to 3 vol. % may cause a carbon dioxide poisoning, which is characterized, for example, by nausea, headache and dizziness. Carbon dioxide concentrations above 12% are immediately lethal. Supply with an insufficient quantity of oxygen may also be harmful for health especially for aviators, pilots or copilots, because the oxygen partial pressure in the blood may be reduced in case of a supply with insufficient quantities of oxygen, and a so-called hypoxic state (hypoxia) develops. Such a reduction of the arterial oxygen partial pressure in the blood—also called hypoxemic hypoxia (hypoxemia)—frequently develops in persons who are at a high altitude. Symptoms of hypoxia are, for example, anxiety and restlessness, dyspnea, cyanosis, tachycardia, an increase in blood pressure, confusion, dizziness, bradycardia and even cardiac arrest.

TECHNICAL BACKGROUND

A device and a process for monitoring inhaled gas is known from EP 3287173 A1. A pressure level of the entire inhaled breathing air and an oxygen partial pressure in the inhaled breathing air are determined during the admission of the breathing air into a face mask of a person and a partial pressure of the oxygen in the lungs of the person is estimated from this. A breathing mask with display device, which is configured to provide data and/or information for aviators, pilots or copilots in a visual form, is known from US 2007181129 A1. The display device is configured as a so-called head-up display. The data and/or information are projected here on the inside onto the visor into the field of view of the aviator, pilot or copilot. Another head-up display is known from U.S. Pat. No. 7,391,574 B2. A face mask with a detection device for ambient temperature and the display and visualization thereof are known from US 2016253561 A. A display device for a face mask in a configuration as a so-called in-mask display is known from US 2019118008 A1. A device for oxygen supply for an airplane, for example, according to the principle of the pressure swing adsorption, is known from U.S. Pat. No. 8,210,175 B2. Oxygen is provided, in addition, from an oxygen reserve. The air is processed with molecular sieve beds, which are scavenged with oxygen from the oxygen reserve at the beginning of the operation. Other devices for oxygen supply in airplanes are known from U.S. Pat. No. 7,407,528 B2, US 2004245390 A1 and U.S. Pat. No. 7,264,647 B2. A compressed air monitoring system for monitoring compressed air with a measuring air line for the continuous sampling of compressed air from a compressed air supply line and with at least one sensor for the continuous detection of at least one parameter of the compressed air is known from DE 102010014222 B4. A sensor for detecting a concentration of carbon dioxide, a sensor for detecting a concentration of nitrogen dioxide, a sensor for detecting a concentration of sulfur dioxide, a sensor for detecting a concentration of oxygen as well as a sensor for detecting a relative humidity of the air in the measured air line are mentioned as sensors for the continuous detection of at least one parameter of the compressed air. EP 2148616 B1 shows a measuring system with a plurality of sensor mechanisms, such as flow sensor mechanism, temperature sensor mechanism, pressure sensor mechanism, humidity sensor mechanism, gas sensor mechanism for the measurement of oxygen, carbon dioxide, carbon monoxide, nitrogen, nitrogen oxides, anesthetic gases, gaseous components in the exhalation as well as other gases. DE 102006030242 A1 shows a configurable measuring system with a plurality of gas sensors. Electrochemical, infrared optical and catalytic gas sensors may be configured as gas sensors in the measuring system. A pump for delivering quantities of air is known from US 20130167843 A1. The pump has a piezoelectric manner of functioning. Such a pump is suitable for delivering quantities of gas from a measuring point to a location of the sensor mechanism and/or measurement-based detection by means of the measured gas line (sample line) and is suitable, for example, for use for a side stream measurement (side stream) for an analysis of gas components, especially also carbon dioxide and oxygen, close to the mouth/nose area of a person or patient for the analysis of inhaled/exhaled air. Many different embodiments and configurations of and with gas delivery devices, pumps or devices for transporting gas for supplying persons with breathing gases, also in embodiments and with suitability for ventilating persons, are known from the patent documents WO 2018033224 A1, US 20180163712 A1, WO 2018033225 A1, US 20180133420 A1, US 20180110957 A1, WO 2019072606 A1, DE 102017009605 A1, DE 102017009606 A1, DE 102018004341 A1 and also DE 202012013442 U1. Other embodiments of gas delivery devices, pumps or devices for transporting gas for supplying persons are known from the German patent applications 102019003643.3, 102019003607.7, 102019004450.9 and 102019004451.7, which have not yet been laid open to public inspection. Many different embodiments and configurations of gas delivery devices, pumps or devices for transporting gas for feeding gases to be measured to a gas measuring device are known from the patent documents DE 102016013756 A1, US 20180143171 A1, US 20180143170 A1 and US 201803354 A1. A connection element, a so-called Y-piece, for connecting ventilation tubes at the mouth/nose area of a person or of a patient with sensor mechanism components, components for measured value acquisition, signal processing, signal analysis and display is known from US 2008264418 A1. The sensor mechanism components comprise a breath flow sensor mechanism with pressure sensor mechanism, a sensor mechanism for measuring the oxygen partial pressure, temperature sensor mechanism, flow rate sensor mechanism, configured as a hot wire anemometer or ultrasonic flow sensor, as well as connection elements for EKG and blood pressure measurement. Oxygen sensors according to the principle of measurement of the so-called luminescence quenching, which may be arranged in the side stream in or at the breathing gas path of a patient, are known from U.S. Pat. No. 7,897,109 B2, U.S. Pat. No. 7,335,164 B2, U.S. Pat. No. 6,616,896 B2, U.S. Pat. Nos. 5,789,660 A and 6,312,389 B1. An oxygen sensor with a bioreactor array is known from DE 102010037923 B4. A system for detecting a reduced oxygen supply in pilots and for reducing the reduction of the oxygen supply in pilots is known from U.S. Pat. No. 9,867,563 B2. A galvanic cell for measuring oxygen is known from US 2003194351 A1. Electrochemical oxygen sensors are known from DE 102004062052 B4 and DE 19726453 C2. An electrochemical sensor for measuring gaseous components in a gas mixture is known from DE 2155935. Many different embodiments of electrochemical gas sensors, which are suitable for a measurement-based detection of oxygen or other gases, are known from U.S. Pat. No. 5,958,200 A, DE 102009010773 B4, DE 102005026491 B4, DE 102005026306 B4 and U.S. Pat. No. 8,496,795 B2. DE 102005007539 A1 shows an electrochemical gas sensor for a quantitative determination of redox-active substances in very low concentration ranges. The electrochemical principle of measurement is suitable, depending on the configuration of the electrodes and of the electrolyte, for the detection of different gases, for example, oxygen, ammonia, sulfur dioxide, hydrogen peroxide, hydrogen sulfide, nitrogen dioxide, nitrogen monoxide, arsine, silanes, formaldehyde, acetylene, carbon monoxide, phosgene, and phosphine. An electrochemical carbon monoxide sensor is known from DE 19912100 A1. An electrochemical carbon dioxide sensor is known from U.S. Pat. No. 4,851,088 A. U.S. Pat. No. 5,473,304 A and DE 4020385 C2 show heat tone sensors manufactured according to ceramic film technology. U.S. Pat. No. 7,875,244 B2, GB 2210980 A1 and DE 19610912 A1 show heat tone sensors of the pellistor configuration. US 2010221148 A1 and U.S. Pat. No. 5,902,556 A show catalytic gas sensors with semiconductor chips as measuring elements. Catalytic gas sensors are known from U.S. Pat. No. 2,816,863 A, US 2019178827 A1, U.S. Pat. No. 8,425,846 B2, U.S. Pat. No. 9,625,406 B2, U.S. Pat. No. 6,756,016 B2, US 2016178412 A1, and U.S. Pat. No. 6,344,174 B1. The catalytic principle of measurement, also called heat tone principle, is especially suitable for detecting combustible and/or explosive gases, especially hydrocarbon compounds, as well as for the determination of residual components of combustion processes. For example, toluene, ammonia, benzene, propane, methane, methanol, octane, butane, ethylene can be detected by measurement based on the heat tone principle. Catalytic sensors are frequently used to monitor limit values, e.g., the LEL (Lower Explosion Limit). U.S. Pat. No. 4,175,422 A shows a gas sensor with a semiconductor element as the measuring element. A gas sensor device with semiconductor sensor mechanism configured according to chip technology for monitoring combustion processes in internal combustion engines of a motor vehicle is known from U.S. Pat. No. 9,958,305 B2. Miniaturized semiconductor gas sensors are known from DE 102004048979 B4 and U.S. Pat. No. 4,902,138 A. A semiconductor type carbon monoxide sensor is known from DE 102012022136 B4. Miniaturized semiconductor oxygen sensors, configured according to the microstructured technology, so-called MEMS (micro-electromechanical system) technology, are known from U.S. Pat. No. 9,818,937 B2 and U.S. Pat. No. 9,234,876 B2. Furthermore, gas sensors with solid electrolytes, e.g., on the basis of zirconium dioxide, are known. Thus, DE 102008056279 B4 shows a device with a heated solid electrolyte oxygen sensor and with an ultrasonic sensor for the indirect detection of the concentration of carbon dioxide. U.S. Pat. No. 5,026,992 A shows a gas sensor for the measurement-based optical detection of methane. U.S. Pat. No. 8,399,839 B2 shows a gas sensor for the measurement-based optical detection of carbon dioxide. A device with a lambda probe for detecting a quantity of residual oxygen in the exhaust gas of an internal combustion engine is known from EP 0149619 A1. A Hall effect oxygen sensor is known from U.S. Pat. Nos. 4,667,157 A. 8,596,109 B2, 9,360,441 B2, 4,808,921 A, 6,430,987 B1, 6,952,947 B2, 6,895,802 B2, 6,405,578 B2, 4,683,426 A, 4,173,975 A, 3,646,803 A, 3,584,499 A, 2,944,418 A and WO 16162287 A1 show devices for measuring concentrations of paramagnetic gases. Especially a qualitative and also quantitative measurement-based detection of oxygen is possible with such devices, because oxygen possesses paramagnetic properties. A measuring element for a paramagnetic gas sensor, especially for an oxygen sensor, is known from U.S. Pat. No. 9,360,441 B2. The paramagnetic gas sensor or oxygen sensor may preferably be arranged in the side stream in or at the breathing gas path of a patient. Gas-measuring devices are described in DE 102010047159 B4 and in US 2004238746 A1. An infrared optical gas-measuring device is described in U.S. Pat. No. 5,739,535 A. An infrared optical carbon dioxide sensor, a so-called IR carbon dioxide sensor, is known from U.S. Pat. No. 8,399,839 B2. Devices for the measurement of the concentration of carbon dioxide in breathing gas by measuring the thermal conductivity are known from DE 102010047159 B4 and U.S. Pat. No. 6,895,802 B2. The configuration according to DE 102010047159 B4 shows a carbon dioxide sensor with a semiconductor chip as a measuring element for detecting changes in thermal conductivity. Infrared optical carbon dioxide sensors are known from U.S. Pat. No. 5,696,379 A, US 2004203169 A1 and U.S. Pat. No. 4,050,823 A. Infrared optical carbon dioxide sensors, which may be arranged in the main stream in the breathing gas path of a patient, are known from U.S. Pat. No. 8,448,642 B2, U.S. Pat. Nos. 5,095,900 A, 5,067,492 A, WO 20109115 A1, US 2019105457 A1, U.S. Pat. No. 6,095,986 A, USD 727492 S and U.S. Pat. No. 5,942,755 A. Gas-measuring devices or sensors for the measurement-based detection of carbon dioxide, especially also suitable for the measurement-based detection of carbon dioxide in breathing gases, are known from US 2002036266 A1, US 2004238746 A1, US 20180120224 A1 and US 20180116555 A1. Other gas-measuring devices or sensors for the measurement-based detection of carbon dioxide are known from the German patent applications 102020114972.7 and 102020114968.9, which have not yet been laid open to public inspection. A combined sensor comprising an infrared optical carbon dioxide sensor with a flow sensor, which may be arranged in the main stream in the breathing gas path of a patient, is known from U.S. Pat. No. 6,571,622 B2. Infrared optical carbon dioxide sensors, which may be arranged in the side stream in or at the breathing gas path of a patient, are known from US 2004238746 A1 and US 2002036266 A1. U.S. Pat. No. 6,954,702 B2, U.S. Pat. No. 7,606,668 B2, U.S. Pat. No. 8,080,798 B2, U.S. Pat. No. 7,501,630 B2, U.S. Pat. No. 7,684,931 B2, U.S. Pat. No. 7,432,508 B2, and U.S. Pat. No. 7,183,552 B2 show gas-measuring systems for detecting gas concentrations in the side stream and in the main stream. Interferometers configured as gas measuring devices are described in U.S. Pat. No. 9,939,374 B2 and U.S. Pat. No. 7,705,991 B2. Laser-based devices for detecting gas components are known from U.S. Pat. No. 6,274,879 B1 and EP 2788739 B1. A gas sensor configured as a photoionization detector is known from U.S. Pat. No. 9,459,235 B2. Other aspects concerning a qualitative and quantitative composition of the breathing gas pertain to the requirement that the breathing gas should be largely free from impurities, for example, it should be largely free from foreign bodies or particles, e.g., soot, dust, pollen or vapors of materials, through which the breathing gas flows on its way to aviators, pilots, copilots and passengers. Furthermore, no or no substantial quantities of gases or gas mixtures that are harmful to health, such as carbon monoxide (CO), ozone, traces of other gases or traces of aviation fuel or kerosene, quantities of exhaust gases or residues of the combustion or other air-borne pollutants shall be present in the breathing gas. These include, for example, many different compositions of hydrocarbons, benzenes, nitrogen oxides ($NO_2$, $NO_x$), sulfur oxides ($SO_2$, $SO_x$), dioxins, furanes, particles, e.g., soot, fine dust, and ultrafine particles. In particular, carbon monoxide poisoning shall also be pointed out, in particular, in this connection in addition to the above-mentioned carbon dioxide poisoning. Even concentrations above 200 ppm (0.02%) cause headache and a loss of judgement, and concentrations above 800 ppm (0.08%) cause dizziness, restlessness, nausea, anxiety and spasms within 45 minutes and loss of consciousness within 2 hours, possibly leading to death. The oxygen transportation capacity of the blood decreases in case of carbon monoxide poisoning due to a reduction of the hemoglobin level (anemia) or due to impairment of the oxygen-binding capacity in the blood, and anemic hypoxia develops.

SUMMARY

Therefore, the need arises to ensure the situation for aviators, pilots, copilots, and passengers that satisfactory and high-quality breathing gas is provided by the on-board equipment of an airplane or aircraft during the flying operation and it can be administered to aviators, pilots, copilots and passengers of airplanes or aircraft. From this arises as an object of the present invention the need to provide a monitoring system for aviators, pilots, copilots and passengers of airplanes or aircraft or to provide a process, which makes it possible to monitor breathing gases and breathing air on the basis of measurements in airplanes or aircraft. From this arises as another object of the present invention the need to provide a process for the measurement-based monitoring of breathing gases and breathing air in airplanes or aircraft.

The object is accomplished, in particular, by a monitoring system for monitoring a gas composition of breathing gases in airplanes or aircraft with the features according to the invention.

The object is also accomplished by a process for operating a monitoring system for monitoring a gas composition of breathing gases in airplanes or aircraft with the features of according to the invention. Further features and details of the present invention and advantageous embodiments appear from the description and from the drawings. References used here refer to the further configuration of the subject of the principal claim by the features of the respective subclaim and they shall not be considered to represent abandonment of the wish to achieve an independent concrete protection for the combinations of features of the referred-back subclaims. Furthermore, it shall be assumed in respect to an interpretation of the claims as well as of the description in case of a more specific concretization of a feature in a dependent claim that such a limitation is not present in the respective preceding claims as well as in a more general embodiment of the concrete system or process. Any reference in the description to aspects of dependent claims shall accordingly also expressly imply a description of optional features even without a special reference. Finally, it shall be noted that the monitoring system being proposed here may also be varied corresponding to the process claims and vice versa, for example, by the monitoring system comprising devices that are intended and/or set up for carrying out one or more process steps or by the process comprising steps that can be carried out by means of the monitoring system or are suitable for operating the monitoring system. Features and details that are described in connection with the monitoring system being proposed for flight crew members or passengers of airplanes or aircraft and of possible embodiments are thus, of course, also valid in connection with and in respect to a process carried out during the operation of the monitoring system and vice versa, so that reference is and can always mutually be made to the individual aspects of the present invention concerning the disclosure.

Embodiments create possibilities for a measurement-based monitoring of the gas composition of air, breathing air or breathing gases in airplanes or aircraft. At least some exemplary embodiments of the present invention pertain to a monitoring system for monitoring the gas composition of air, breathing air or breathing gases in airplanes or aircraft. At least some exemplary embodiments of the present invention pertain to a monitoring system for monitoring the gas composition of air, breathing air or breathing gases in airplanes or aircraft. At least some exemplary embodiments of the present invention pertain to a process for operating a monitoring system for monitoring the gas composition of air, breathing air or breathing gases in airplanes or aircraft. A measurement-based detection of properties of at least one gas may be made possible by means of a sensor mechanism of a monitoring system in at least some exemplary embodiments. Properties of a gas may include, for example, physical and other properties: Pressure, density, viscosity, thermal conductivity, electrical and magnetic properties, temperature, gas composition, moisture content, toxicity, calorific value, combustibility, binding capacities with other gases or liquids, for example, water or blood. A qualitative measurement-based detection of at least one gas may be made possible in at least some exemplary embodiments. A quantitative measurement-based detection of at least one gas and/or of a concentration of a gas may be made possible in at least some exemplary embodiments. A qualitative and a quantitative measurement-based detection of at least one gas may be made possible in at least some exemplary embodiments. A qualitative and a quantitative measurement-based detection of oxygen may be made possible in at least some exemplary embodiments. A qualitative and a quantitative measurement-based detection of carbon dioxide may be made possible in at least some exemplary embodiments. A qualitative and a quantitative measurement-based detection of another gas, especially carbon monoxide, may be made possible in at least some exemplary embodiments.

A control unit is arranged in the monitoring system or is associated with the monitoring system in at least some exemplary embodiments. The control unit is configured and intended to organize, to control or to regulate a course of a measurement-based monitoring of the gas composition of air, breathing air or breathing gases in airplanes or aircraft. The control unit is preferably configured from components (ρC, μP, PC) with corresponding operating system (OS), memory (RAM, ROM, EEPROM) as well as SW code, software for process control, control, and regulation. In at least some exemplary embodiments, additional electronic components, for example, components for signal detection (ADμC), signal amplification, for analog and/or digital signal processing (ASIC), components for analog and/or digital signal filtering (DSP, FPGA, GAL, μC, μP), and signal conversion (A/D converter) are assigned to the control unit or are connected to the control unit in at least some exemplary embodiments.

In at least some exemplary embodiments, a qualitative and a quantitative measurement-based detection of a concentration of oxygen may be made possible in at least some exemplary embodiments. The concentration of oxygen may be determined in this case by measurement, for example, in the form of a partial pressure in a gas mixture of, for example, the breathing air or of the breathing gas or in the form of a volume concentration or in the form of a mass per unit volume. In at least some exemplary embodiments, a qualitative and a quantitative measurement-based detection of a concentration of carbon dioxide may be made possible by means of the sensor mechanism in at least some exemplary embodiments. The concentration of carbon dioxide may be determined in this case by measurement, for example, in the form of a partial pressure in a gas mixture, for example, of the breathing air or of the breathing gas or in the form of a volume concentration or in the form of a mass per unit volume. In at least some exemplary embodiments, a qualitative and a quantitative measurement-based detection of a concentration of carbon monoxide may be made possible by means of the sensor mechanism. The concentration of carbon monoxide may be determined in this case by measurement, for example, in the form of a partial pressure in a gas mixture, for example, of the breathing air or of the breathing gas or in the form of a volume concentration or in the form of a mass per unit volume. The sensor mechanism may have at least one sensor in at least some exemplary embodiments. The at least one sensor is preferably configured in this case as an oxygen sensor, as a carbon dioxide sensor or at least one additional gas sensor, especially carbon monoxide sensor. In at least some exemplary embodiments, a paramagnetic oxygen sensor or a measuring module with a paramagnetic oxygen sensor may be used for the qualitative and quantitative measurement-based detection of the concentration of oxygen. An electrochemical oxygen sensor may be used in this case in another advantageous manner. An oxygen sensor or a measuring module with an oxygen sensor, which operates according to the principle of luminescence quenching or fluorescence quenching, may be used in this case in another advantageous manner. A semiconductor oxygen sensor, preferably in the form of a so-called MEMS oxygen sensor or a measuring module with a semiconductor oxygen sensor or with a MEMS oxygen sensor, may be used in this case in another advantageous manner. An electrochemical oxygen sensor and/or paramagnetic oxygen sensor or a measuring module with an electrochemical oxygen sensor and/or with a paramagnetic oxygen sensor may be used in this case in another advantageous manner. An electrochemical oxygen sensor and/or a semiconductor oxygen sensor or a measuring module with an electrochemical oxygen sensor and/or with a semiconductor oxygen sensor may be used in this case in another advantageous manner. A paramagnetic oxygen sensor and/or a semiconductor oxygen sensor and/or with an electrochemical oxygen sensor or a measuring module with a paramagnetic oxygen sensor and/or with a semiconductor oxygen sensor and/or with an electrochemical oxygen sensor may be used in this case in another advantageous manner. A paramagnetic oxygen sensor and/or a semiconductor oxygen sensor or a measuring module with a paramagnetic oxygen sensor and/or with a semiconductor oxygen sensor may be used in this case in another advantageous manner. An optical carbon dioxide sensor, preferably in the form of an infrared optical, a so-called IR carbon dioxide sensor, or a measuring module with an optical, preferably infrared optical carbon dioxide sensor, with a so-called IR sensor, may be used in at least some exemplary embodiments for the qualitative and quantitative measurement-based detection of the concentration of carbon dioxide. A semiconductor carbon dioxide sensor, preferably in the form of a so-called MEMS carbon dioxide sensor or a measuring module with a semiconductor carbon dioxide sensor or with a MEMS carbon dioxide sensor may be used in this case in another advantageous manner. A semiconductor carbon dioxide sensor, preferably in the form of a so-called MEMS carbon dioxide sensor and/or an optical carbon dioxide sensor, preferably in the form of an infrared optical, so-called IR carbon dioxide sensor or a measuring module with a semiconductor carbon dioxide sensor or a MEMS carbon dioxide sensor and/or with an optical carbon dioxide sensor or IR carbon dioxide sensor may be used in this case in another advantageous manner.

The measuring modules with at least one oxygen sensor are also called oxygen measuring modules in the context of the present invention. The measuring modules with at least one carbon dioxide sensor are also called carbon dioxide measuring modules in the context of the present invention.

The oxygen measuring modules and/or carbon dioxide measuring modules may also have additional sensors in some embodiments or additional sensors may also be associated with the oxygen measuring modules and/or carbon dioxide measuring modules in some embodiments and/or such additional sensors may be arranged at the modules. The oxygen measuring module and/or the carbon dioxide measuring module may optionally be configured in some embodiments such that they are combined with additional gas sensors and optionally with additional sensors for the measurement-based detection of measured variables or substance parameters, for example, pressure, ambient pressure, airway pressure, mask pressure, density, temperature, thermal conductivity, thermal capacity, volume flow, mass flow, flow rate, volumes, or they are configured as an environmental or ambient analysis module. Thus, a pressure sensor in the monitoring system may be arranged, for example, as a component of the oxygen measuring module or of the carbon dioxide measuring module, which is configured to detect a pressure level in the measured gas line. In addition, a flow sensor or flow rate sensor in the monitoring system may be arranged, for example, as a component of the oxygen measuring module or of the carbon dioxide measuring module, which is configured for the detection of a flow rate or of a flow in the measured gas line. Measured values of the flow sensor, flow rate sensor as well as of the pressure sensor may be made available to the control unit.

In some embodiments, the monitoring system or such modules as gas measuring modules, measuring modules, environmental or ambient analysis modules, may have at least one gas transport module. The gas transport module has to this end a gas delivery device, preferably a pump, with a gas port, which gas delivery device is configured to deliver a defined quantity of gas from a measuring point located at a distance from the sensor mechanism or from the oxygen measuring module, carbon dioxide measuring module or gas measuring module to the oxygen measuring module, to the carbon dioxide measuring module or to the gas measuring module or to the oxygen sensor or to the carbon dioxide sensor in order for the measurement-based detection of the oxygen concentration and/or carbon dioxide concentration to be made possible. The pump or the gas transport module is configured such as to suck in quantities or partial quantities of breathing gas or breathing air from a measuring point, especially from the breathing mask and/or from the cabin or from the cockpit and to deliver it to the monitoring system or to the oxygen measuring module and/or to the carbon dioxide measuring module or to the sensor mechanism, especially to the oxygen sensor and/or to the carbon dioxide sensor. The breathing mask may be configured, for example, as a partial mask, half mask or full mask or as a combination of a safety helmet with a mask. Valves may additionally be arranged in the incoming flow in front of the pump or in the outgoing flow behind the pump in order to largely or completely prevent back flows or to avoid unintended flows or flowthrough. The gas transport module is preferably connected pneumatically and/or fluidically to the measuring point in a gas-carrying manner preferably by means of a measured gas line (sample line). A gas-carrying component is preferably used as a measuring point in the area of the face, i.e., close to the mouth/nose area of the aviator, pilot or copilot to monitor the breathing gas supply of the aviator, pilot or copilot. One end of the measured gas line is preferably arranged at the mouth/nose area, for example, at the breathing mask, in order to make possible a flow of quantities of gas from the mouth/nose area to the gas transport module of the monitoring system. The other end of the measured gas line is preferably connected pneumatically or fluidically to a gas port for an incoming flow into the gas transport module such that a delivery of quantities of gas or of partial quantities of breathing gas is made possible, for example, at a flow rate in the range of 25 mL/min to 250 mL/min by means of the gas transport module to the oxygen measuring module and/or to the carbon dioxide measuring module. The gas transport module is connected to this end pneumatically and/or fluidically to an additional gas port for the outgoing flow or delivery to the oxygen measuring module and/or to the carbon dioxide measuring module. The control unit can control the gas transport module by means of the flow sensor or flowthrough sensor and it can control, regulate or set the quantities of gas to be delivered or to be sucked in in the measured gas line. The control unit can monitor the pressure level in the measured gas line by means of the pressure sensor and it can also control, regulate or set it by means of the gas transport module. If the flowthrough sensor is configured as a pressure difference sensor GP sensor) of a difference measurement of two pressure measurement points over a flow diaphragm, a pressure measurement of the pressure level in the measured gas line can also be made possible with this sensor with the detection of one of the two pressure measurement points with reference to the environment.

In a preferred embodiment, the gas transport module in the form of a pump may be arranged at a gas inlet of the monitoring system. In such an exemplary constellation, the gas transport module sucks in quantities of gas through the measured gas line from the breathing mask of the aviator into the monitoring system and it then delivers these quantities of gas to and through the sensor mechanism for the determination of the gas concentration. After flowing through the sensor mechanism, the quantities of gas enter into the environment through a gas outlet.

In another preferred embodiment, the gas transport module in the form of a pump may be arranged at a gas outlet of the monitoring system. In such an exemplary constellation, the gas transport module sucks quantities of gas through the measured gas line from the breathing mask of the aviator into the monitoring system through the sensor mechanism for the determination of the gas concentration. After flowing through the pump, the quantities of gas enter the environment through a gas outlet. With the pump being arranged at the gas outlet, possible contaminants cannot reach the sensor mechanism through the pump. Quantities or partial quantities of breathing gas can be transported via the gas transport module, especially the pump, via the pneumatic and/or fluidic connection to the oxygen measuring module and/or to the carbon dioxide measuring module or to the oxygen sensor and/or to the carbon dioxide sensor, so that a measurement-based detection of concentrations of oxygen and/or carbon dioxide is made possible. The monitoring system is configured in such a construction that it can be arranged in or at the clothing of the aviator, pilot or copilot. The measured gas line has a corresponding length, so that such an arrangement is made possible. Accommodation or arrangement of the monitoring system in a breast pocket, leg pocket or thigh pocket of a flight suit (aviator overall) is especially advantageous. The gas delivery module is configured and constructed such that quantities of gas can be delivered from the measuring point to the preferred location of arrangement in a breast pocket, leg pocket or thigh pocket of the flight suit. The gas transport module may be configured, for example, as a centrifugal pump, axial pump, radial pump, reciprocating pump or a diaphragm pump. A pump with low energy consumption is especially advantageous for use in the monitoring system for mobile and energy-self-sufficient use. A piezoelectrically operated pump, also often called piezo pump, makes possible, for example, an energy-saving use for gas concentration measurement in the monitoring system. Such a pump is available commercially, for example, from Murata Manufacturing Corp. of Kyoto, Japan, as a so-called "piezoelectric blower" or "microblower" with the names MZB1001T02 as well as MZB 1001. These pumps do not block the flow even without electrical actuation or activation, and it is therefore advantageous in case of use for the monitoring system to provide a valve, which ensures the flow in the measured gas line in a reliable and reproducible manner and unambiguously with two states, namely, "release" and "blockage." A shut-off valve, a so-called "flow-lock valve," which may preferably be arranged at the gas outlet, is advantageous for the embodiment with the pump at the gas outlet as well as for the embodiment with the pump at the gas inlet. The arrangement of the shut-off valve at the gas outlet of the monitoring system makes possible the use of the pressure sensor arranged in the interior of the monitoring system for determining the pressure in the breathing mask of the aviator by means of a measurement maneuver to determine the pressure in the breathing mask, because the pressure level in the interior of the monitoring system corresponds to the pressure level in the measured gas line as well as to the pressure level in the breathing mask with the shut-off valve closed in the no-flow state. A reversing valve, a so-called "3/2-way valve," which may preferably be arranged at the gas inlet, is advantageous, as an alternative, for the embodiment with the pump at the gas inlet. This reversing valve makes it possible, on the one hand, to feed quantities of gas from the measured gas line into the monitoring system, and, on the other hand, it can thus also be made possible to feed quantities of gas from the environment, i.e., from the cabin of the aircraft. The control unit can simultaneously determine the pressure level in the breathing mask by means of a measurement maneuver for determining the pressure in the breathing mask during the feed of quantities of gas from the cabin.

An additional gas port with a reversing valve is arranged in the monitoring system in a preferred embodiment. An additional gas port with a reversing valve is arranged in or at the gas transport module in another preferred embodiment. This reversing valve makes possible a switching between a feed of quantities of gas from the measured gas line and a feed of quantities of gas by means of the additional gas port from the environment, for example, from the cabin of the aircraft. In another preferred embodiment, an additional pump is arranged in or at the additional gas port. This additional pump makes it possible to feed quantities of gas by means of the additional gas port from the environment, for example, from the cabin of the aircraft. In addition to the shut-off valve at the gas outlet, an optional reversing valve may be arranged at the gas inlet for switching between a monitoring of quantities of gas from the measured gas line from the breathing mask and of quantities of gas from the cabin for the embodiment with the pump at the gas outlet. Thus, the control unit is then enabled to carry out at any time a switching between the feed of quantities of breathing gas from the breathing mask of the aviator and a feed of gas from the cabin independently from times at which the pressure in the mask is determined.

The control unit may be configured in some embodiments to determine breathing phase information, i.e., a duration in time of an inhalation, a duration in time of an exhalation, a ratio (I:E ratio) of the duration of inhalation to the duration of exhalation, as well a respiratory frequency of the aviator, pilot or copilot, from the measured values of the carbon dioxide sensor.

The sensor mechanism and the control unit may be configured in at least some exemplary embodiments to detect at least one environmental parameter and/or at least one operating parameter. Operating parameters may be, for example, parameters from the flying operation, parameters from the supply of the aviator, pilot or copilot with breathing gases, parameters from the control and regulation of the aircraft or of components of the aircraft. In at least some exemplary embodiments, the sensor mechanism and the control unit may be configured to also take into account at least one environmental parameter and/or to also include it in the process during the control of the measurement-based monitoring process.

The control unit is configured in a preferred embodiment in conjunction and together with a pressure sensor to determine a current pressure level in the breathing mask. The aviators (pilots, copilots) are supplied by means of a breathing mask arranged at the mouth/nose area during the flying operation of a jet airplane (jet). The monitoring of the current pressure level in the breathing mask of the aviator, pilot or copilot is therefore of particular interest. It can thus be ensured that a sufficient pressure level of breathing gas is made available by means of the breathing mask for the aviator, pilot or copilot.

Embodiments show possibilities of configuring a detection of pressure levels in the breathing mask by means of the sensor mechanism and of the control unit and of thus monitoring, providing, outputting and/or documenting the pressure level in the breathing mask. The control unit detects a pressure level in the measured gas line by means of a pressure sensor, which is arranged in the monitoring system connected pneumatically and fluidically in a pneumatic system to the components breathing mask, measured gas line, connection elements and an HME filter element optionally arranged in a series connection in the measured gas line to detect a pressure measured value, which indicates a pressure level in the pneumatic system. In another preferred embodiment for detecting the current pressure level, a pressure measurement is initiated by the control unit in a measurement situation during the operation of the monitoring system, in which no quantities of gas are fed from the breathing mask to the sensor mechanism with the gas transport module deactivated and with the pump deactivated, i.e., the gas concentration measurement by the sensor mechanism is interrupted or paused at times. The measured value, which indicates the pressure level in the pneumatic system, corresponds in such a measurement situation to the current pressure level in the breathing mask. In addition to the deactivation of the pump, the shut-off valve can be brought into a closed state in order to prevent any exchange of gas of the pneumatic system with the environment. A measurement and checking of the pressure level in the breathing mask can be carried out intermittently with such an embodiment if the feed of quantities of gas by the pump is deactivated at defined time intervals.

A pressure measurement is initiated by the control unit in another preferred embodiment for detecting the current pressure level during the ongoing operation of the monitoring system, in which quantities of gas are continuously fed from the breathing mask to the sensor mechanism. A measurement and checking of the pressure level in the breathing mask can be carried out with such an embodiment continuously if an adaptation or calibration to pressure drops of the pneumatic system, which change during the operation, is carried out with the components breathing mask, measured gas line, connection elements and the HME filter element intermittently at different time intervals. An adaptation or calibration, which can be carried out intermittently or at defined time intervals, may be configured in such a preferred embodiment by a measurement maneuver, which is coordinated and carried out by the control unit in interaction with the gas transport module or the pump, the shut-off valve and a memory. Such a measurement maneuver may be carried out from time to time during the flying operation in order to continuously determine changes in or at the pneumatic system at defined times in the time course of the operation of the monitoring system during the mission at the aviator. The measurement maneuver comprises a measurement-based detection of pressure levels for zeroing or for offset determination at two working points. The measurement maneuver is divided into a pressure measurement of a static pressure level at a working point without a gas flow in the pneumatic system and into a measurement-based detection of a dynamic pressure level in the form of a measurement at another predefined working point with a defined flow in the pneumatic system. A pressure measured value is detected during the measurement-based detection of the static pressure level without gas flow within the pneumatic system with the components breathing mask, measured gas line, connection elements and an HME filter element optionally arranged in the measured gas line in a series connection. Without a gas flow, i.e., with the pump shut off and with a resulting flow rate of 0.00 mL/min, no pressure drops caused by components will occur in the pneumatic system between the breathing mask and the pressure sensor or the pump in the monitoring system. The HME filter element is used to prevent moisture from the breathing gas supply with breathing tube and breathing mask, which moisture is introduced into the measured gas line by the exhalation of the aviator during the operation, from entering into the monitoring system for monitoring a gas composition of breathing gases. Such an HME filter element (HME=Heat Moisture Exchange) is configured to retain quantities of moisture. The HME filter element is arranged in a preferred embodiment in the measured gas line, at the gas inlet or at the gas transport module. Due to the exhalation of moist breathing gases by the aviator, quantities of moisture or liquid will continuously accumulate during the operation in the HME filter element. This leads to changes in the flow resistance over the duration of the use during the flying operation with the monitoring system operating. In addition to the switching off of the pump, the shut-off valve will advantageously be brought into a closed state in order to prevent any gas exchange of the pneumatic system with the environment. The detected pressure measured value without gas flow in the measured gas line corresponds to a snapshot of the current pressure in the breathing mask with the shut-off valve closed and it is stored as a static pressure of the pneumatic system in a memory. A pressure measured value with a defined quantity of a gas flow with pressure drops corresponding to this gas flow at the components of the pneumatic system with measured gas line, with connection elements and with the optional HME filter element is detected at the time of the measurement-based detection of the dynamic pressure level. The detected pressure measured value with a defined quantity of a gas flow is stored as a dynamic pressure of the pneumatic system in the memory. A range of 10 mL/min to 400 mL/min can be activated, controlled or regulated by the control unit as a suitable and defined quantity of the gas flow in the measured gas line. The pressure measured value with flow corresponds to the dynamic current total pressure drop of the pneumatic system. This pressure measured value then corresponds to the sum of the pressure drops in the pneumatic system, i.e., with pressure drops over the components such as breathing mask, HME filter element, measured gas line and connection elements. The control unit can determine from the difference of the previously determined static pressure level and the sum of the dynamic pressure drops the pressure drop attributed to the components as an offset pressure level in the pneumatic system. Changes in the differences determined between the dynamic and static pressure measured values between two or more times at which the measurement maneuver is carried out make it possible for the control unit to draw conclusions concerning changes in the pressure drops and changes in the offset pressure level in the pneumatic system during the operation. These offset pressure levels in the pneumatic system and their differences as well as their changes are detected or determined continuously during the flying operation by the control unit and are stored in the memory, for example, in the form of a data set or of a table or as a log file. The control unit is advantageously configured by means of the measurement maneuver in this preferred embodiment to determine, subsequently to provide, to output and/or to store, in the form of data sets or tables, offset pressure levels determined by a measurement-based detection of static and dynamic pressure drops over the pneumatic system as calibration values for a determination of the current mask pressure. Thus, the measurement maneuver provides trends and changes of the offset pressure level during the operation of the monitoring system at the aviator, pilot or copilot during the mission. It is possible in this manner to determine and to monitor the particular, currently occurring mask pressure of the aviator even among components of the pneumatic system which change during the flying operation. In particular, an increase in the pressure drop over the HME filter element, which is due to moisture saturation, can be detected as a change in the offset pressure level by continual repetitions of the measurement maneuver and it can be compensated in the calculation of current pressure levels in the breathing mask. Such repetitions of the checking may take place, for example, once every 15 minutes to 60 minutes, and a more frequent performance is not advantageous because the monitoring concerning the gas concentrations is interrupted or paused for a short time for the performance of the maneuver. The determination of the current pressure in the breathing mask can also be carried out by the control unit during the operation with the pump activated and with measurement-based detection of the gas concentrations of oxygen and/or carbon dioxide as well as possibly other gases or the cabin air on the basis of a use of the offset pressure level of the components of the pneumatic system, which offset pressure level was determined last with the measurement maneuver. The current pressure level present in the breathing mask is obtained by subtracting the last determined offset pressure level, which is stored in the memory and is the last determined offset pressure level provided there, from the current pressure measured value obtained during the flow through the measured gas line. The measurement maneuver, which was already described before for determining the pressure in the breathing mask, will also be explained in respect to the integration of this measurement maneuver into the measuring operation of the monitoring system for the measurement-based detection of the gas concentration, preferably of carbon dioxide and oxygen, with the functions of the components involved in that process. The measurement maneuver can be activated or started at predefined times from the ongoing measuring operation of the monitoring system. The following steps are activated, initiated and carried out by the control unit in a sequence of steps from a start to an end:

a deactivation of the pump is carried out in a first step, the shut-off valve is closed in a second step,
a first measuring operation is carried out in a third step by the pressure sensor with a pressure measurement to determine the static pressure level,
the shut-off valve is opened in a fourth step,
the pump is activated in a fifth step to deliver quantities of gas at a defined flow rate in the range of 50 mL/min to 100 mL/min from the breathing mask through the measured gas line into the monitoring system to the sensor mechanism; the flow rate is controlled and monitored in the process by a flow measurement by means of the flowthrough sensor,
another measuring operation is carried out in a sixth step by the pressure sensor, i.e., a pressure measurement is carried out to determine the dynamic pressure level, and
a determination of a difference value is carried out in a seventh step with the pressure measured values of the first pressure measurement and of the additional pressure measurement.

The difference value thus determined represents the offset pressure level and can be provided and used as a calibration value for the determination of a mask pressure during the further operation of the monitoring system during the mission of the aircraft. In optional embodiments of the sequence of steps of the measurement maneuver, the measurement-based detections of the static and dynamic pressure level and/or of the flow rates can be carried out by the control unit in the third, fifth and sixth steps synchronized with the breathing of the aviator, pilot or copilot. The pressure measurements and/or the flow measurements can thus preferably be carried out during inspiratory or expiratory pauses.

In a preferred embodiment, the control unit may be configured to also take information concerning breathing phases of the aviator into account during the measurement-based detection and/or determination of the static pressure measured value and/or of the dynamic pressure measured value during the carrying out of the measurement maneuver to determine the pressure in the breathing mask. The detection of the pressure measured values with a synchronization with the breathing with performance of the measured value acquisition during pauses between inhalation and exhalation is advantageous because no pressure effects due to the breathing, which are superimposed to the static and/or dynamic pressure levels, can make unfamiliar or influence the pressure measured value. The synchronization with the breathing can be carried out by the control unit by means of breathing phase information based on changes in the concentrations of carbon dioxide and/or oxygen, which changes are detected by measurement in the monitoring system. The physiological concentration differences in the oxygen content in the breathing gas between inhalation (21%) and exhalation (16%) as well as concentration differences in the carbon dioxide content between exhalation (~5%) and inhalation (<1%) can be used by the control unit to determine breathing phases. Without such synchronization of the pressure measurement, a suitable signal filtering, for example, by means of low-pass filtering or—preferably sliding—mean value formation of the measured values of the pressure sensor, is useful in order to remove the components of the breathing or of the respiratory rate from the pressure measured values.

Provisions can therefore be made in an especially preferred embodiment for the control unit to be configured, together with the signal processing with the use of suitable signal filtering, to determine the static and/or dynamic pressure measured values with removal of signal components induced by the breathing of the aviator by means of signal filtering. A gas analysis of the cabin air can advantageously be carried out with the use of the reversing valve during the time during which the mask pressure is determined. Predefined values (set points), reference values as threshold values of the breathing mask pressure can be provided by an external system, for example, via a data interface. The monitoring system can then determine an alarm generation situation on the basis of such values in case of values above or below the threshold values and provide corresponding alarm signals and/or data. Such a provision may be carried out, for example, in a wired manner, in a wireless manner by means of radio transmission, in a wireless manner by means of infrared transmission to external systems. Further possibilities for generating an alarm for the aviator are offered by visual, optical or acoustic signal generation systems, such as lamps, light-emitting diodes, display units, speakers, buzzers, horns or comparable elements. Another possibility for alarm generation for the aviator may be tactile alarm generation, for example, in the form of a vibration alarm.

Additional embodiments can show how additional environmental parameters may be able to be determined by the control unit in addition to the mask pressure. Environmental parameters include during the operation of airplanes or aircraft, for example, ambient pressure outside the cockpit or cabin of the airplane or aircraft,
ambient temperature within the cockpit or cabin of the airplane or aircraft,
gas composition within the cockpit or cabin of the airplane or aircraft,
absolute and/or relative humidity within the cockpit or cabin of the airplane or aircraft,
density and/or ambient pressure within the cockpit or cabin of the airplane or aircraft,
ambient temperature within the cockpit or cabin of the airplane or aircraft,
gas composition within the cockpit or cabin of the airplane or aircraft,
ambient pressure outside the cockpit or cabin of the airplane or aircraft, ambient temperature outside the cockpit or cabin of the airplane or aircraft, gas composition outside the cockpit or cabin of the airplane or aircraft, absolute and/or relative humidity outside the cockpit or cabin of the airplane or aircraft, density and/or ambient pressure outside the cockpit or cabin of the airplane or aircraft, ambient temperature outside the cockpit or cabin of the airplane or aircraft, gas composition outside the cockpit or cabin of the airplane or aircraft, pressure level, pressure changes, pressure changes over time, pressure differences, pressure fluctuations in the breathing gas, breathing gas mixture or in the breathing air in the feed line to the aviator, pilot or copilot, and pressure level, pressure changes, pressure differences, pressure fluctuations in the on-board equipment provided (e.g., gas tanks, pressurized oxygen cylinders, air intake, gas treatment, filtering) for breathing gas, breathing gas mixture or breathing air.

The control unit may be configured in at least some exemplary embodiments also to take into account at least one situational parameter during the control of the course of the measurement-based monitoring and/or to include it in the procedure. Situational or current situational parameters are defined as situations and/or states arising from situations during the operation of airplanes or aircraft.

These include, for example:
a flight direction,
a flight altitude,
a flight axis position,
a flight position,
for example, inverted flying, curve flight, nosedive, descent, ascent,
a flight velocity,
a horizontal acceleration,
a vertical acceleration,
a yaw angle or a roll angle,
a residual oxygen or air reserve, and
a residual reserve of pressurized oxygen or compressed air.

The monitoring system may have a data interface in some embodiments. The data interface may be configured as a unidirectional or bidirectional data interface and may be configured, for example, for data supply, data reception, data exchange or communication with components of the airplane or aircraft.

The situational parameters and/or the ambient parameters may be received and/or provided in at least some exemplary embodiments by the monitoring system and/or by the control unit by means of the data interface. In at least some exemplary embodiments, the situational parameters and/or the ambient parameters may be detected by measurement by means of additional sensors of the sensor mechanism, which are arranged in or at the monitoring system, and be made available to the control unit. Additional gas sensors, for example, for the measurement-based detection of carbon monoxide as well as additional gas sensors, e.g., in the form of electrochemical gas sensors, catalytic gas sensors, optical, infrared optical gas sensors, photoionization gas sensors, solid electrolyte gas sensors or semiconductor gas sensors may be used for this purpose in the sensor mechanism in addition to the sensor mechanism for the measurement-based detection of oxygen and/or carbon dioxide, in order to make it possible to monitor the breathing gas in addition to the measurement-based detection of concentrations of oxygen and carbon dioxide with respect to other substances as well, such as hydrocarbons, residues or products of combustion processes. All additional sensors in the sensor mechanism may also be provided by pressure sensors, which may be configured to detect an ambient pressure from the environment, especially a pressure or a density within and/or outside the cockpit or cabin of the airplane or aircraft by measurement and to make it available to the control unit. The additional sensors in the sensor mechanism may be configured as temperature sensors, which may be configured and intended for detecting an ambient temperature of the environment, especially a temperature inside and/or outside a cockpit or cabin of the airplane or aircraft, by measurement, and to make it available to the control unit. These additional sensors in the sensor mechanism may be configured as humidity sensors for detecting an absolute or relative humidity of the environment, which may be configured or intended to detect a humidity in the environment, especially inside and/or outside a cockpit or cabin of the airplane or aircraft and to make it available to the control unit.

In some embodiments, additional sensors at/in the sensor mechanism in the monitoring system may be provided for detecting data to determine the situational parameters or they may be associated with the sensor mechanism, which make it possible for the control unit to determine a current flight situation with flight altitude, flight direction, flight velocity, flight acceleration, flight position with orientation in space and flight situation or flight maneuver (e.g., ascent, descent, curve flight, approach for landing, start). For example, pressure sensors, acceleration sensors, altitude sensors, compass sensors, gyro sensors, humidity sensors, and temperature sensors are arranged for this purpose at or in the sensor mechanism or are associated with the sensor mechanism.

The sensor mechanism may be arranged in some embodiments very close to the mouth/nose area in or at the breathing mask. Depending on the fluidic conditions at the mouth/nose area, an active transport of breathing gases to the sensor mechanism may be eliminated in such cases. The breathing gases reach the sensor mechanism passively, i.e., by diffusion from the mouth/nose area in the mask. Integration of the sensor mechanism into the breathing mask in or at parts of the breathing mask may be made possible in special configurations. Due to the progress being made in technological development in the area of chip and/or MEMS technology, miniaturization of elements of the electrochemical, catalytic or semiconductor sensor mechanisms can be expected in the near future, and this will then be able to make possible an integration of the sensor mechanism, preferably oxygen sensor mechanism, carbon dioxide sensor mechanism and other gas sensors as well as of additional and optional pressure sensor mechanisms and/or temperature sensor mechanisms directly at the measuring point.

An additional gas port may be provided at the gas transport module in some embodiments. The additional gas port makes it possible to connect and to feed quantities or partial quantities of gas or ambient air from the cabin or the cockpit to the monitoring system. Gas, quantities or partial quantities from the ambient air or from the mouth/nose area of the aviator, pilot or copilot, for example, from the breathing mask can be fed as desired to the pump or to the gas transport module via a reversing valve (e.g., a 3/2-way valve) or a system of valves.

An additional pump may be provided in some embodiments and it may be arranged such that a pump for transporting gas, quantities or partial quantities from the ambient air to the oxygen measuring module and/or to the carbon dioxide measuring module or to the oxygen sensor and/or to the carbon dioxide sensor is provided and arranged and this additional pump is intended and arranged for transporting gas, quantities or partial quantities from the mouth/nose area of the aviator, pilot or copilot, for example, from the breathing mask, to the oxygen measuring module and/or to the carbon dioxide measuring module or to the oxygen sensor and/or to the carbon dioxide sensor. A reversing valve (e.g., a 3/2-way valve) or a system of valves for switching between quantities or partial quantities of breathing gas can thus be eliminated in such an embodiment.

The control unit may be configured in some embodiments to control the gas transport module. A control of the gas transport module may comprise in this case an activation, a deactivation, a setting, a control or a regulation of the gas transport module. The setting may comprise especially a setting of speed of rotation, flow rate and/or pressure level, for example, by means of optical or electrical control signals (CAN bus, PWM) or electrical control voltages. A determination concerning a leak present in the measured gas line can also be carried out in one variant of such embodiments on the basis of the detection of gas concentration values and/or pressure measured values, for example, also on the basis of pressure differences between the mask and the cockpit.

The control unit may further be configured in some embodiments also to take into account and/or to include in the control at least one ambient parameter or at least one situational parameter in the control of the gas transport module. Such a taking into account may comprise especially an adaptation of activation, deactivation, speed of rotation, flow rate and/or pressure level of the gas delivery module. It can thus be made possible to deactivate the gas transport module during certain flight maneuvers, for example, during an ascent, descent or curve flight and/or optionally to activate it with an increased flow rate after the end of the maneuver.

In at least some exemplary embodiments, the monitoring system and/or the control unit may be configured for a determination and/or detection of an alarm situation and for organizing an alarm generation or for sending an alarm and/or for providing an alarm signal. The control unit can determine and/or detect an alarm situation and trigger an alarm generation and/or provide an alarm signal, for example, at the data interface or at another data interface on the basis of measured values of the sensor mechanism and/or by means of information provided for the data interface. The alarm generation may take place as a visual and/or acoustic and/or tactile alarm generation. A visual alarm generation may take place, for example, in the form of a white and/or colored lighting device (LED, stroboscope) or of a text output (LCD, LED, display). Such an alarm generation may also be carried out visually by means of a suitable visualization device at or in a face mask or breathing mask, for example, as a display on an in-mask display or head-up display. An acoustic alarm generation may be carried out, for example, in the form of a speech output or by means of an acoustic alarm generator (horn, siren). A tactile alarm generation may be carried out, for example, in the form of a vibration alarm to equipment of the aircraft, such as seat surfaces, control elements (pedals, handles) as well as pieces of equipment (breathing mask, breathing tube) or clothing (suit, vest, parachute, shoes) of the aviator, pilot or copilot.

In some embodiments, the control unit can also take into consideration an ambient parameter and/or a situational parameter and/or include it in the organization of the alarm generation during the organization of the alarm generation or alarm and/or during the provision of the alarm signal. It can thus be made possible in an advantageous manner that relevant alarm information, which is prioritized according to relevance, can be provided for the aviator, pilot or copilot in a consolidated or compact manner concerning the situation of the measurement-based detection in the breathing gas with reference to the situation in the environment (temperature, gas composition in the breathing air) and in reference to the mission situation or to maneuver situation of the airplane (start phase, landing approach, in-flight refueling, descent, curve flight, ascent). In a special embodiment, the control unit can also take into consideration an ambient parameter and/or a situational parameter and also include it in an adaptation of the signal processing during the performance of the signal processing and/or signal filtering of the measured values of the sensor mechanism.

In some exemplary embodiments, the control unit can use during the organization of the alarm generation predefined threshold values, which may be stored for certain values of gas concentrations, especially concentrations of oxygen or carbon dioxide or carbon monoxide, in the memory of the monitoring system.

On the basis of current concentration measured values, which were obtained in the past and are in the form of a trend monitoring of oxygen and carbon dioxide, and by means of a suitable decision matrix or algorithms specially adapted to the problem, teachable or self-learning algorithms (SVM, Random Forest, AI, Deep Learning, PCA), the control unit can apply in some embodiments a kind of early warning system for detecting hypoxia, possibly with an alarm management adapted to this for the onset of a developing hypoxia. In a special situation, the control unit can also take into consideration an ambient parameter and/or a situational parameter. In a special embodiment, the control unit may also take into consideration in the early warning system for the detection of hypoxia additional physiological data of aviators, pilots and copilots, for example, EKG, heart rate, heart rate variability, oxygen saturation in the blood, body temperature, which data were assigned, for example, by means of the data interface or by the monitoring system.

In some embodiments, such modules as gas measuring modules, measuring modules, environmental or ambient analysis modules, may have at least one energy storage device, e.g., a primary cell or a rechargeable battery. For example, types of lithium ion batteries, nickel-metal hydride batteries or nickel-cadmium batteries are known as types of rechargeable batteries. For example, types of alkali-manganese batteries, silver oxide-zinc batteries, lithium batteries and aluminum-air batteries are known as types of primary cells.

Battery charging systems and/or battery management systems for monitoring battery charge and/or battery state as well as interfaces for supplying the battery charging systems and/or battery management systems with charging electrical energy may usually also be integrated additionally in the monitoring system in embodiments with rechargeable batteries. Battery management systems usually have interfaces for communication to the outside, in order, for example, to be able to provide data or information on the state of the battery, and such interfaces may have a wired (e.g., CAN bus), contactless (e.g., RFID, NFC), wireless (e.g., Bluetooth) or infrared optical (e.g., IrDA) configuration. In addition, such modules as gas measuring modules, measuring modules, environmental or ambient analysis modules may have additional components, for example, components for signal detection (AD$\mu$C), signal amplification, for analog and/or digital signal processing (ASIC); components for analog and/or digital signal filtering (DSP, FPGA, GAL, $\mu$C, μP), signal conversion (A/D converters), components (μC, μP) for controlling, regulating, components (μC, μP) for process control of the operation and for user interaction; input and output interfaces, user interface with at least one operating element and/or with at least one display element. The at least one operating element as well as the at least one display element may be arranged in or at the monitoring system or may be associated with the monitoring system.

For example, an operation with beginning (start, activation) or end (stop, deactivation) of the monitoring system, a selection between different modes of operation of the monitoring system, performance of maintenance, adjustment or calibration processes can be made possible for the user in some embodiments by means of the at least one operating element.

The user can be enabled in some embodiments by means of the at least one display element to be informed of events, situations, current measured values and/or measured values obtained in the past, which were detected and provided by measurement by means of the sensors or measuring modules, especially of the oxygen sensors and/or of the carbon dioxide sensors or of the oxygen measuring modules and/or carbon dioxide measuring modules. In addition, measured variables derived from the measured values, for example, maximum or minimal values, mean values, trends, statistics, events, alarm situations, may be provided for the user by means of the display elements. In addition, general information on the current operating state of the monitoring system, such as the state of the battery, residual battery life, maintenance information, information on the monitoring system itself, such as type, name, variant, version, serial number, initial start-up, expected maintenance intervals, status data, operating state (ready, in-OP, Stand-by), information on malfunctions, error memory, as well as operating instructions, may be provided for the user by means of the display elements.

The display elements may be configured as graphic user interface (graphical user interface, GUI) in some embodiments.

In addition to the display elements, input elements may be provided in some embodiments. The input elements may be configured as mechanical or touch-sensitive buttons or switches, rotary controls or slide controls as well as in the form of a graphic user interface (graphical user interface, GUI). Display elements may be configured in some embodiments such that they are combined with input elements. In an embodiment with a touch-sensitive display (touch screen), there are, for example, possibilities for designing changeable display possibilities and operating possibilities, e.g., a use of gestures (wiping, pulling) in order thus to vary the type of the display, for example, in order to enlarge or to reduce display elements (zoom function). The combination of display elements with input elements may preferably be configured as a graphic user interface (graphical user interface, GUI, touch pad).

It is possible in some embodiments to provide an input element, which makes it possible for the user or operator of the monitoring system to initiate, annotate, trigger, start or end defined actions or states at the monitoring system. Such an input element may be configured, for example, as an annotation button and/or as a panic button, which can preferably be operated by actuation by hand. As an alternative, operation with speech command may also be possible, in which case the annotation button and/or the panic button is equipped correspondingly with devices for speech detection, speech processing and speech recognition with command detection.

The input element may also be complemented in other alternative embodiments by an acceleration sensor or may be configured by such an acceleration sensor. For example, data or measured values of an acceleration sensor, which is provided as a component of an additional sensor mechanism at/in the sensor mechanism in the monitoring system for detecting data for determining situational parameters, may also be used for this purpose by the control unit in order to detect by measurement a current flight situation with flight altitude, flight direction, flight velocity, flight acceleration, flight position with orientation in space and flight situation or flight maneuvers (e.g., ascent, descent, curve flight, landing approach, start) in the monitoring system. As an alternative, an additional 2-axis or 3-axis acceleration sensor, which represents a functionality of an input element in conjunction with the control unit, may be arranged in or at the monitoring system. Movements or excursions of the monitoring system, movements or excursions of a housing of the monitoring system, as well as mechanical, tactile stimuli or tactile stimulations can be detected by means of sensors by means of the acceleration sensor and they can be made available as measured values or data to the control unit. Mechanical or tactile stimuli or stimulations are sent from the aviator, pilot or copilot to the acceleration sensor as a force action, energy feed or force feed in the direction of at least one of the directions or axes detectable in a sensor-based manner by the acceleration sensor in the form of actuation acting on the monitoring system by means of movements of the hand, in the form of application of pressure, in the form of the action of an impact (push, hit, tapping). This is made advantageously possible for the aviator, pilot or copilot especially if the monitoring system is arranged as a mobile module in a closed pocket in or on the clothing, for example, on or in a vest, jacket or a suit. The force feed may thus take place as an actuating activity through the clothing to the acceleration sensor in the monitoring system. The use of the acceleration sensor as an input device or input element makes possible an actuation or operation of the monitoring system by the aviator, pilot or copilot during the mission when he cannot reach other input elements at the monitoring system configured as a mobile module. This happens, for example, when the monitoring system is arranged as a mobile module in a pocket in or on the clothing. The acceleration sensor thus offers an alternative to an operation of the monitoring system by means of a manual button or of a manual switching element. A control unit may be used for the analysis of the measured values or data of the acceleration, but it is also possible to provide an additional unit, which is equipped in the monitoring system to detect and analyze data of the acceleration sensor. Such an analysis of the data of the acceleration sensor is based essentially on time measurements. An analysis can be carried out by means of time measurements in conjunction with threshold values for the measured values or data of the acceleration sensor concerning the duration of the tactile stimulation as well as concerning durations between two or more tactile stimulations of the acceleration sensor. The control unit may be configured in an exemplary embodiment to detect a first-time force action or force feed to the acceleration sensor by means of a comparison with a threshold value on the basis of the measured values or data of the acceleration sensor. If a measured value of the acceleration sensor is exceeded in respect to a predefined threshold value for a first predefined duration, the control unit interprets this situation as a first force action in the direction of at least one of the directions or axes detectable in a sensor-based manner by the acceleration sensor. An indicator is thus obtained for a start of an input activity of the aviator by means of a movement of the hand as an input operation. If the measured values of the acceleration sensor are subsequently exceeded once again for a second predefined time period for a second predefined threshold value, the control unit interprets this situation as the end of the first force action. If a measured value of the acceleration sensor is then exceeded within a third predefined duration in respect to the first predefined threshold value for the first predefined duration, the control unit interprets this situation as a further force action in the direction of at least one of the directions or axes detectable in a sensor-based manner by the acceleration sensor. An indicator is thus obtained for a continuation of the input activity of the aviator. If values below the second predefined threshold value are then obtained for a second predefined time period from measured values or data of the acceleration sensor, the control unit interprets this situation as the end of the further force action. If no further force actions on the acceleration sensor are detected and recognized within a fourth predefined duration, an indicator is obtained for the end of the input activity of the aviator. With this type of analysis the control unit is configured and able to detect and recognize an input activity of a "double tap" by a movement of the hand of the aviator by means of an analysis of the measured values of the acceleration sensor concerning the first and second threshold values and of the first, second, third and fourth durations during the operation of the monitoring system and it can then trigger further actions based on this in or at the monitoring system. Such actions may correspond in terms of their manner of functioning, for example, to functions of an annotation button and/or of a panic button.

In addition to the "double tap," the configuration of the control unit may be expanded in respect to the analysis in some embodiments such as to make possible inputs by a "triple tap" or "quadruple tap" as well. A simple coding is obtained in this manner for inputs effected by means of the acceleration sensor, so that the control unit can make a distinction between different input situations by means of a case differentiation between "double tap," "triple tap" or "quadruple tap." It is also possible, in principle, to configure a "single tap," and the duration of the stimulation, which the "single tap" indicates, would be set now in such a manner that possibilities of confusion with other stimulations by the aviator, the aircraft or the equipment are ruled out.

In addition to the analysis of durations of the tactile stimulations, the configuration of the control unit may additionally also include in the analysis in some embodiments differences of durations between the tactile stimulations of the acceleration sensor. These differences can then be used by the control unit, in addition to analyses of forms of "multiple tapping," to increase the number of events that can be distinguished from one another, for example, by a distinction between a "short pause" and a "long pause" as durations between the tactile stimulations of the acceleration sensor. A type of Morse code is thus obtained due to this variation of pause lengths during the analysis of the tactile stimulations, which offers a further possibility for coding events with the acceleration sensor as the input element.

Possibilities and advantages are consequently obtained due to the fact that when different input situations are distinguished with assignment to acts or actions triggered with the input, the aviator, pilot or copilot can start, for example, a measurement maneuver by hand with the acceleration sensor as the input element during the flying operation, he can make an entry (annotation) or set a time mark in a log book or can mark a special health situation, e.g., a sensation of dizziness during the data recording or data storage, without having to operate a button or switch at the monitoring system with visual contact with the monitoring system. A measurement maneuver may be, for example, a measurement maneuver to determine static and dynamic pressure levels in the pneumatic system or a measurement maneuver to activate the reversing valve to detect gas concentrations in the cabin.

In some embodiments, a memory for storing measured values of measured variables derived from measured values, for example, maxima or minima, mean values, trends, statistics, events and alarm situations may be arranged in or at the monitoring system or may be associated with the monitoring system. Such a memory may be configured as a volatile or non-volatile memory (RAM, ROM, EEPROM) and may be configured either as a fixed component of the monitoring system or also as a removable and/or portable memory module (USB stick, SD card). The memory may be used for data recording or data storage of inputs made by means of the input element and provide to this end functions of a log book or flight recorder. In an embodiment with tables, lists and data sets, the log book may advantageously receive an analysis of gas concentration measured values, flow measured values, pressure measured values, temperature measured values over time with assignment to a time and marking (annotation), further events or manual inputs by means of the input element and keep them available and provide them for a simultaneous or subsequent analysis. When the events are entered, measured values or measured signals of the acceleration sensor may be added in order to put the respective marks/notation made in the log book by the pilot into a context with flight situations or with flight maneuvers for a real-time or later analysis. When entering the events, measured values or measured signals of an altitude sensor may be added in order to put the respective marks/notation made by the pilot in the log book into a context with flight situations (flight altitude) for a real-time or later analysis. When entering the events, measured values or data of the gas sensor mechanism may be added in order to put the mark/notation made by the pilot in the log book into a context with the gas supply ($CO_2$, $O_2$) for a real-time or later analysis.

In a special configuration of some embodiments, the control unit may be configured to also take into consideration an environmental parameter and/or a situational parameter when the signal processing and/or signal filtering is carried out and/or to include it in the adaptation of the signal processing.

The control unit may be configured in some embodiments to use predefined threshold values, which may be stored for defined values of gas concentrations, especially concentrations of oxygen or carbon dioxide and carbon monoxide, in the memory of the monitoring system during the organization of the alarm generation.

The control unit may be configured in some embodiments to employ an early warning system for the detection of hypoxia on the basis of current and past measured values of the sensor mechanism, for example, in the form of a trend monitoring of concentrations of oxygen and/or carbon dioxide,
   by means of a decision matrix,
   or by means of specially adapted algorithms, and
   or by means of teachable or self-learning algorithms (e.g.,
      SVM, Random Forest, AI, Deep Learning, ICA, PCA).

The control unit may also take into account in this case an environmental parameter and/or a situational parameter in special configurations of some embodiments.

In other special configurations of some embodiments, the control unit may use an alarm management adapted to the early warning system. In a special configuration of some embodiments, the control unit may be configured to take into consideration further physiological data of aviators, pilots and copilots, which were provided, for example, by means of the data interface or by the monitoring system, for example, EKG, heart rate, heart rate variability, oxygen saturation in the blood and body temperature, in the early warning system for the detection of hypoxia.

Further exemplary embodiments create processes for the operation of a monitoring system.

In some embodiments of the process for operating a monitoring system, the control unit performs in a first step an activation of the sensor mechanism of the monitoring system, and preparations are made for data storage along with initialization of a memory in a second step. Measurement-based detection of measured values of the sensor mechanism of the monitoring system is carried out with a time control in a third step. Data storage of the measured values is carried out in the memory with corresponding time information in a fourth step. The third and fourth steps are continued continuously by the control unit until the process for operating a monitoring system is ended.

In some embodiments of the process for operating a monitoring system, an additional storage of situational parameters and/or environmental parameters can be made possible during the data storage of the measured values of the sensor mechanism with the corresponding time information in the memory.

In some embodiments of the process for operating a monitoring system, an additional detection of measured values of the sensor mechanism, which detection depends on the time control, can be made possible when an input element is activated by a user.

Further actions improving the present invention appear from the following description of some exemplary embodiments of the present invention, which are shown in the figures. All the features and/or advantages, including design details and arrangements in space, which appear from the claims, from the description or from the drawings, may be essential for the present invention both in themselves and in the different combinations. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Figure 1A:
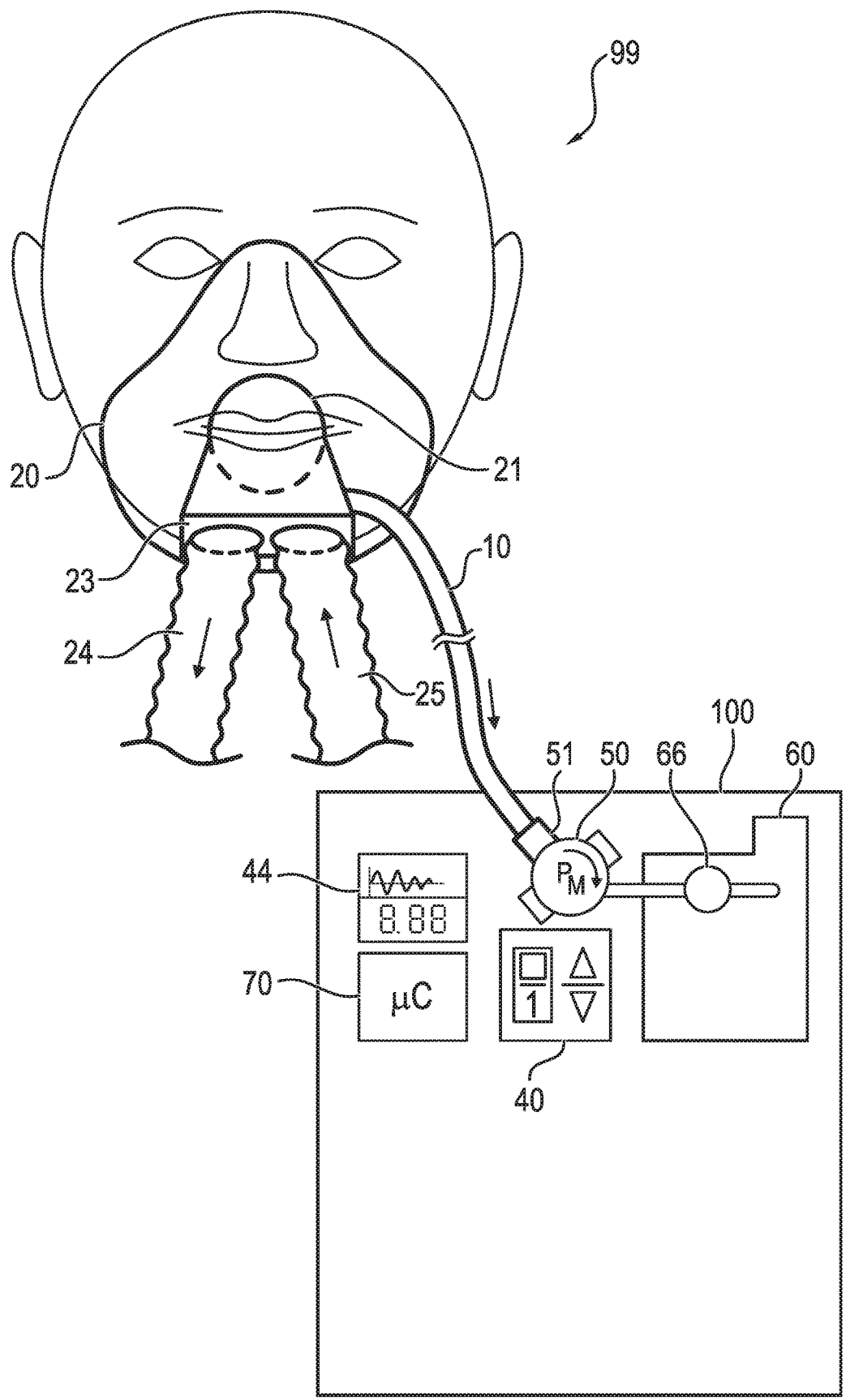
FIG. 1a is a schematic view showing a monitoring system with a sensor mechanism.
Figure 1B:
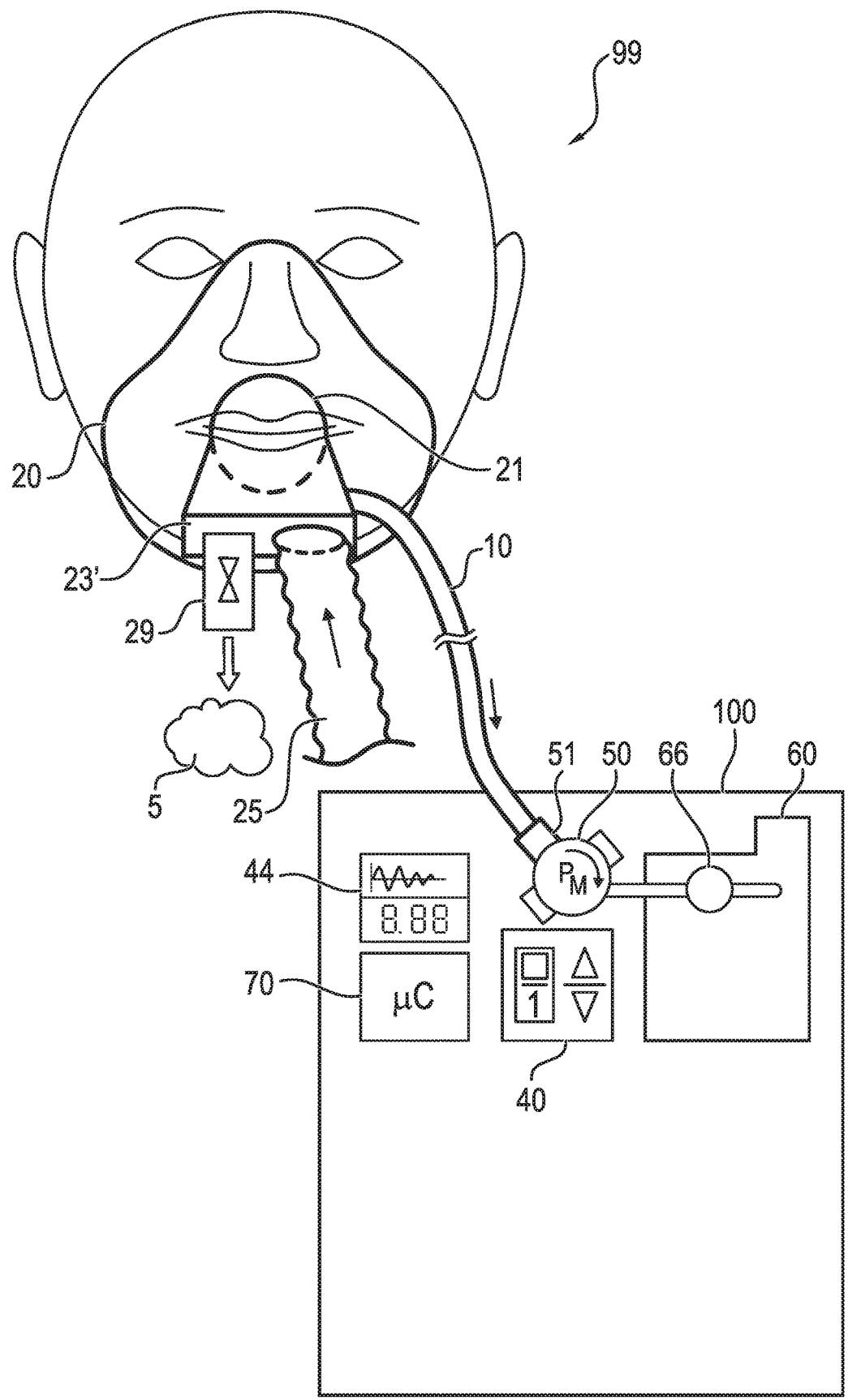
FIG. 1b is a schematic view showing the monitoring system with a sensor mechanism.

Referring to the drawings, FIGS. 1a, 1b show a monitoring system 100, which is connected with a measured gas line 10 to a breathing mask 20 of a person 99. Identical elements in FIGS. 1a, 1b are designated by the same reference numbers in FIGS. 1a, 1b. The person 99 in this FIG. 1 is an aviator (pilot, copilot) or passenger of an airplane, especially of a jet plane (jet). The breathing mask 20 has a gas port 21, a connection element 23 as well as hose lines 24, 25. The hose lines 24, 25 are used to remove and feed breathing gases to the person 99. The hose lines are shown in this FIG. 1a as two separate hose lines 24, 25. As is shown in FIG. 1b, embodiments with a connection element 23', in which embodiments only one hose line 25 is present for supplying breathing gas for inhalation, and the exhalation takes place via an exhalation valve 29 in the breathing mask 20 to an environment, are also possible. Another possibility is offered by an embodiment of a coaxial hose system, which has two hose lines 24, 25 as a common element. The removal and feed of breathing gases into the airplane or aircraft and the devices or elements necessary therefor for making the breathing gas available are not shown in this FIG. 1a and in the other figures for the sake of clarity. The monitoring system 100 has operating elements 40, display elements 44, at least one gas delivery module 50, and a sensor mechanism 60 with at least one sensor 66. The gas delivery module 50 is preferably configured as a pump PM, more preferably as a piezoelectric pump PM. In addition, the monitoring system 100 has a control unit 70.

The operating elements 40, the display elements 44, the sensor mechanism 60, and the gas delivery module 50 are connected to the control unit 70 via signal and data lines or control lines. These control lines or signal and data lines may be configured, for example, as a bus system (CAN) or network. These control lines or signal and data lines are not shown in FIG. 1a as well as in the other figures for the sake of clarity. The control unit 70 is configured and intended to control and/or to actuate the gas delivery module 50 such that a delivery of breathing gases from the breathing mask 20 through the measured gas line 10 and through a gas inlet 51 to the sensor mechanism will take place. A quantity or partial quantity of breathing gas is thus then available to the at least one sensor 66 in the gas sensor mechanism 60 in order to detect it by measurement and/or to analyze it and to make it available to the control unit 70 as measured values. The control unit 70 makes it possible to analyze and process the measured values and to display them at least on partial elements of the display elements 44.

Figure 2A:
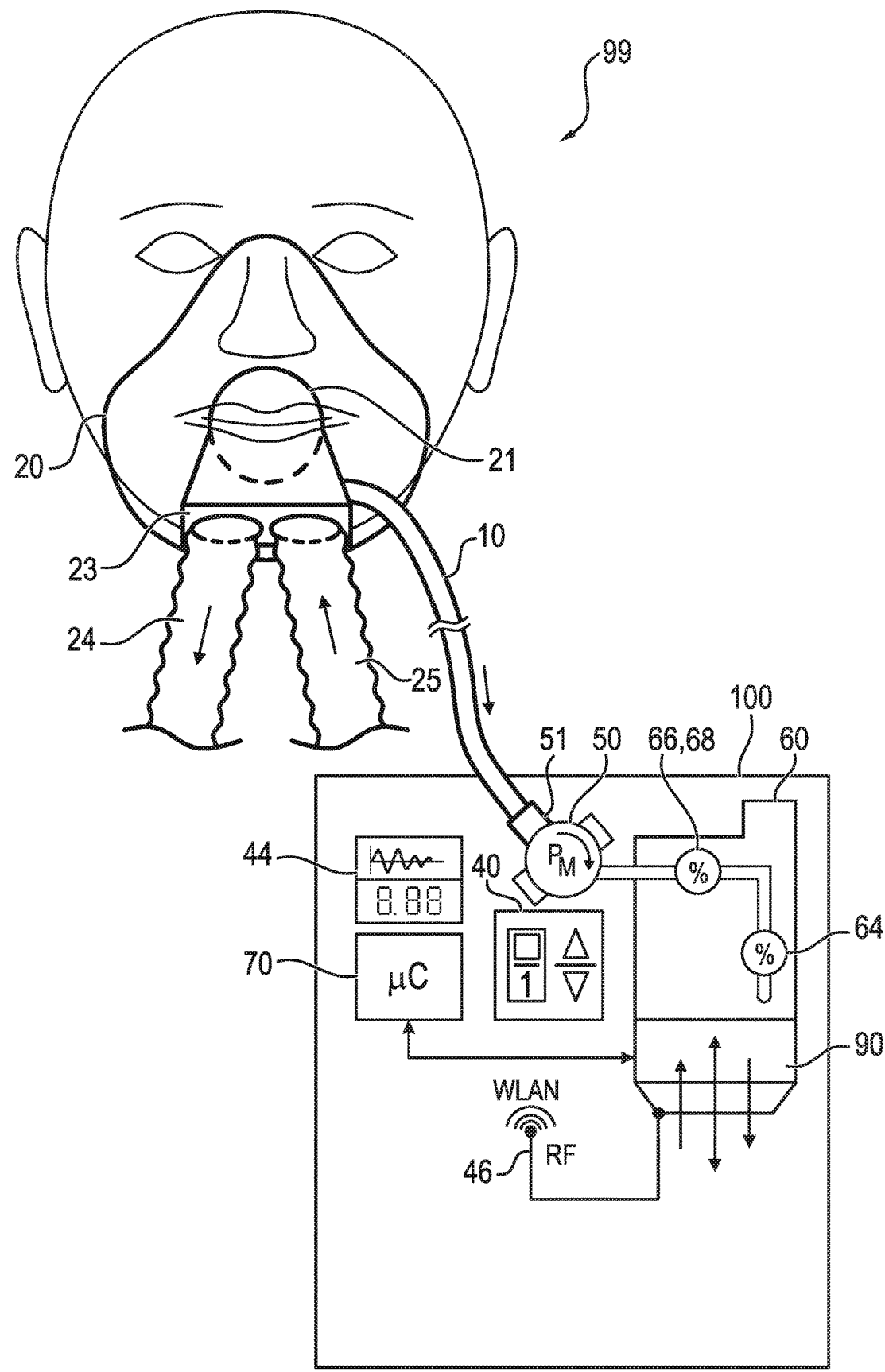
FIG. 2a is a schematic view showing a monitoring system according to FIG. 1a, 1b with a measurement functionality for oxygen and carbon dioxide.
Figure 2B:
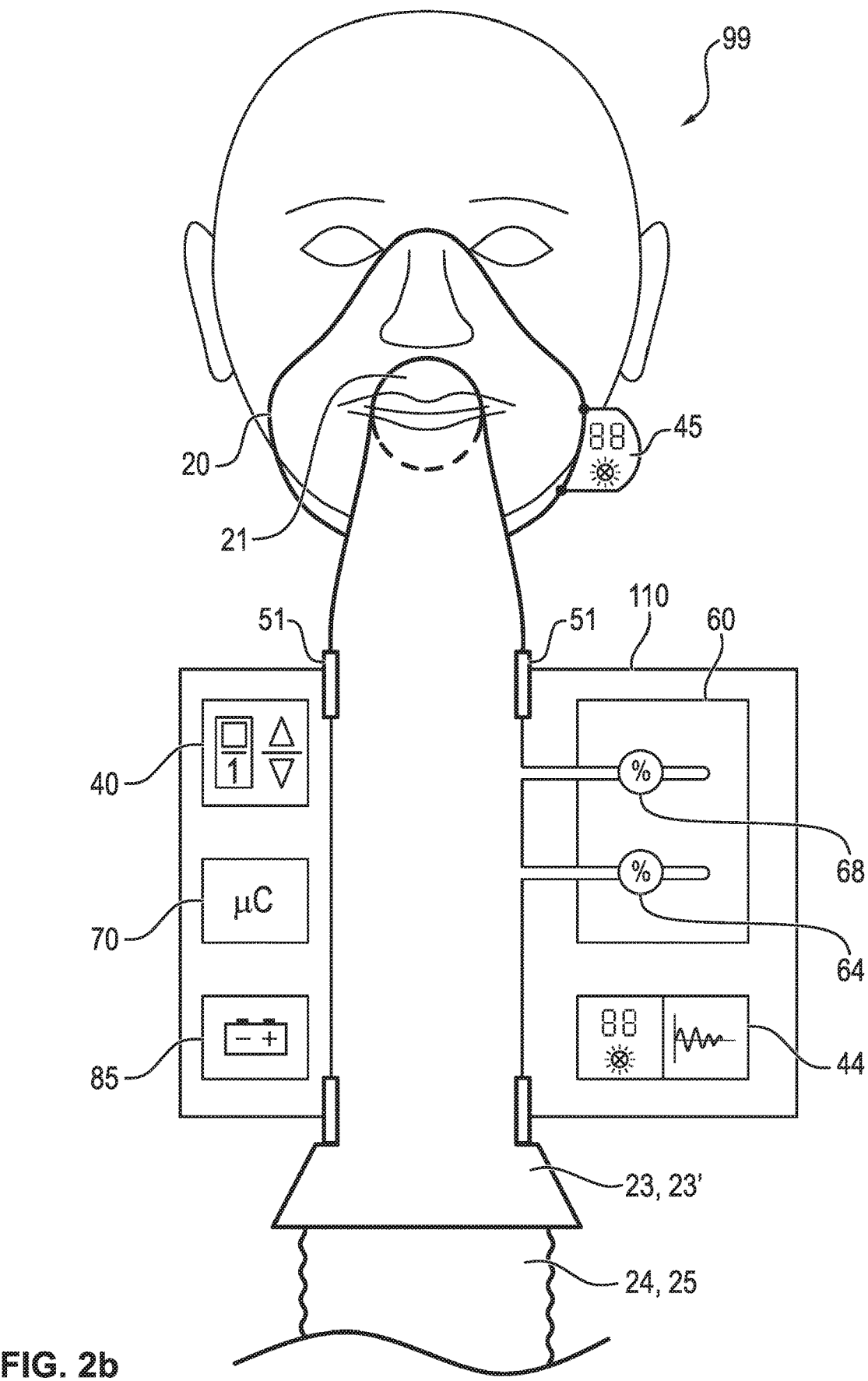
FIG. 2b is a schematic view showing a monitoring system according to FIG. 1a, 1b with the measurement functionality for oxygen and carbon dioxide.

FIGS. 2a, 2b show monitoring systems 100, 110 according to FIGS. 1a, 1b with the peculiar feature that the sensor 66 in the sensor mechanism 60 is configured as an oxygen sensor 68 and, in addition, an additional sensor acting as a carbon dioxide sensor 64 is likewise arranged in the sensor mechanism 60. Identical elements in FIGS. 1a, 1b, 2a, 2b are designated by the same reference numbers in FIGS. 1a, 1b, 2a, 2b. FIG. 2a shows a variant 110 of a monitoring system according to FIG. 2a with an oxygen sensor 68 and with a carbon dioxide sensor 64, wherein the monitoring system 110 is arranged without a measured gas line 10 directly at the breathing mask 20 or is configured as a part of the breathing mask 20. A pump PM, as in the variants according to FIGS. 1a, 1b, 2a for delivering quantities of breathing gas from the breathing mask 20 to the sensor mechanism 60 may optionally be eliminated. In case quantities of gas are optionally also to be delivered from the cabin or from the cockpit to the sensor mechanism, an optional pump 56 is also arranged in or at the sensor mechanism in the arrangement according to FIG. 2b. The arrangement of such an optional pump 56 in the monitoring system 110 is not shown for the sake of clarity. An energy storage device 85 is also shown as an example in FIG. 2b, and it is also an optional component of the embodiments according to FIGS. 1a, 2a, 3, 4, 5 in a similar configuration. Such an energy storage device 85, configured as a primary cell or chargeable or rechargeable battery (rechargeable battery, storage battery), has a suitable configuration for supplying the various components (60, 70, 40, 44, 75) of the monitoring systems 110, 108 (FIG. 4), 109 (FIG. 5), 100 (FIG. 1a, FIG. 1b, FIG. 2a, FIG. 3) with electrical energy. An optional embodiment with an additional display element 45 arranged at or in the mask 20 is shown in FIG. 1b, and there also is a similar configuration as an optional component of the configurations according to FIGS. 1a, 2a, 3, 4, 5. This additional display element 45 is connected to the control unit 70 by means of signal or data lines, not shown for the sake of clarity. This additional display element may be configured, for example, in the form of an in-mask display or head-up display. FIG. 2a additionally shows a data interface 90, which may be configured, on the one hand, to receive data from the outside and then to provide these data for the control unit 70. The data lines belonging to the data interface are not shown in FIG. 2a as well as in the other figures for the sake of clarity. On the other hand, for example, measured values of the monitoring system 100 or of the sensor mechanism 60 can be sent to the outside by means of the data interface 90. Current environmental parameters or situational parameters on the situation of the airplane or aircraft can thus be received via this data interface 90, for example, from components of the airplane or aircraft, and made available to the control unit 70 for being taken into consideration in the processing of measured values and/or in the control of the pump PM 50. Furthermore, measured values and/or measured variables derived from the measured values or parameter as well as information or state data may be made available by the control unit 70 by means of the data interface to components of the airplane or aircraft. It is possible in this manner, for example, to display measured values and/or measured values derived from the measured values or parameters as well as information or state data on external display elements of the airplane or aircraft. The data interface may have a unidirectional or bidirectional configuration, for example, a wired (CAN bus, LAN, Ethernet, RS485, NMEA183) or wireless (WLAN, Bluetooth, NFC) configuration. The following parameters shall be mentioned, for example, as current environmental parameters for an environmental situation of the airplane or aircraft:

ambient pressure outside the cockpit or cabin of the airplane or aircraft,
ambient temperature within the cockpit or cabin of the airplane or aircraft,
gas composition within the cockpit or cabin of the airplane or aircraft,
absolute and/or relative humidity within the cockpit or cabin of the airplane or aircraft,
density and/or ambient pressure within the cockpit or cabin or the airplane or aircraft,
ambient temperature within the cockpit or cabin of the airplane or aircraft,
gas composition within the cockpit or cabin of the airplane or aircraft,
ambient pressure outside the cockpit or cabin of the airplane or aircraft,
ambient temperature outside the cockpit or cabin of the airplane or aircraft,
gas composition outside the cockpit or cabin of the airplane or aircraft,
absolute and/or relative humidity outside the cockpit or cabin of the airplane or aircraft,
density and/or ambient pressure outside the cockpit or cabin of the airplane or aircraft,
ambient temperature outside the cockpit or cabin of the airplane or aircraft,
gas composition outside the cockpit or cabin of the airplane or aircraft,
pressure level, pressure changes, pressure-time curve, pressure differences, pressure fluctuations in the breathing gas, breathing gas mixture or in the breathing air in the feed line to the aviator, pilot or copilot,
pressure level, pressure changes, pressure differences, pressure fluctuations in the on-board equipment provided (e.g., gas tanks, pressurized oxygen cylinders, air intake, gas processing, filtering, gas delivery) for breathing gas, breathing gas mixture or breathing air.

For example, the following parameters shall be mentioned as situational or current situational parameters of the situation of the airplane or aircraft:
a flight direction,
a flight altitude,
a flight axis position,
a flight position,
for example, inverted flying, curve flight, nosedive, descent, ascent,
a flight velocity,
a horizontal acceleration,
a vertical acceleration,
a yaw angle or a roll angle,
a residual oxygen or air reserve, and
a residual pressurized oxygen gas or compressed air reserve.

Figure 3:
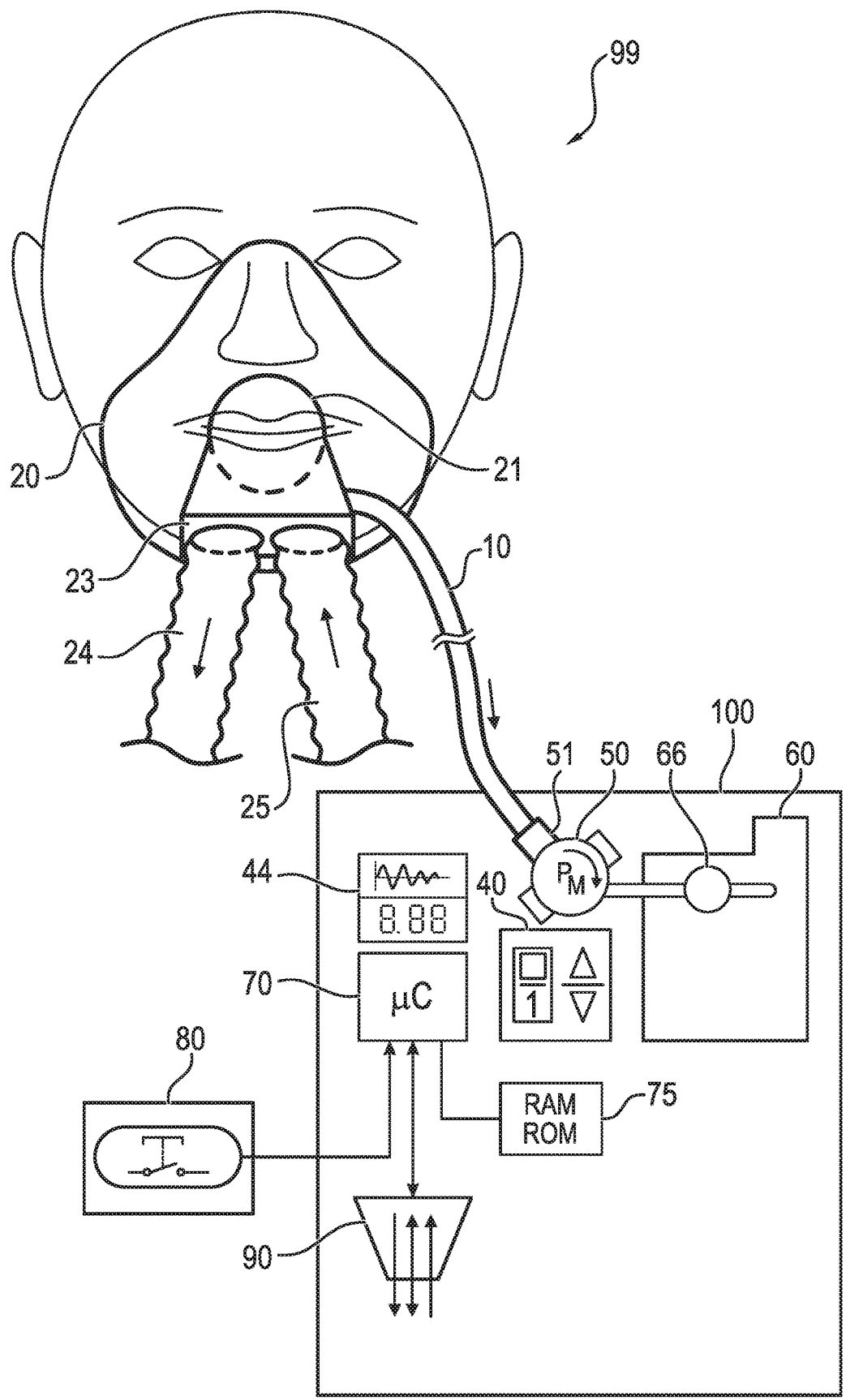
FIG. 3 is a schematic view showing an expansion of the variants according to the monitoring systems according to FIGS. 1a, 1b, 2a, 2b.

FIG. 3 shows a monitoring system 100 according to FIG. 1a, 1b, 2a with the peculiar feature that an input element 80 with a signal or data connection to the control unit 70 is arranged at the monitoring system. Identical elements in FIGS. 1a, 1b, 1c, 2, 3 are designated by the same reference numbers in FIGS. 1a, 1b, 1c, 2, 3. It is made possible to the aviator, pilot or copilot via the input element 80 to mark certain events or situations of the flying operation, as well as certain personal events, for example, events, situations or symptoms related to health, such as fever, racing heart or a feeling of dizziness, during the course of the mission. This marking can be used by the control unit 70 to combine the events or situations with time information and then to store the combination of time information, event or situation in a memory 75. The memory 75 may be configured as a volatile or non-volatile memory (RAM, ROM, EEPROM) and be arranged either as a fixed component or as a removable memory module (USB stick, SD card) in or at the monitoring system 100, 110 (FIG. 2b). A provision and/or an exchange of the data may also be made possible with an external analysis unit, not shown in the figures, for example, by means of a data interface 90 in a configuration similar to that shown and described in FIG. 2b. This input element 80 can thus be used to complement the detected measured values of the sensor mechanism 60 and the events and situations of the flying operation by additional information, which is made available by means of the input element of the aviator, pilot or copilot, and to provide it with time information, for example, in the form of a time stamp. It is also possible, however, to configure the input element as a panic button, which makes it directly possible to the aviator, pilot or copilot to make themself noticeable in a situation that is a special situation based on his own perception, for example, in a situation with a special, objectively or subjectively perceived danger situation or in a risk situation. The marked measured values and/or events, situation and also the special situations can be made directly available to the direct external outside environment for example, by means of the data interface 90, and they can possibly be transmitted, likewise directly (on-line), via a communication system of the airplane or aircraft, to a ground station or to other airplanes or aircraft. Furthermore, an analysis of the marked measured values and/or events, situations and special situations later after the mission (off-line) can be made possible by means of the memory 75 and/or the data interface 90.

Figure 4:
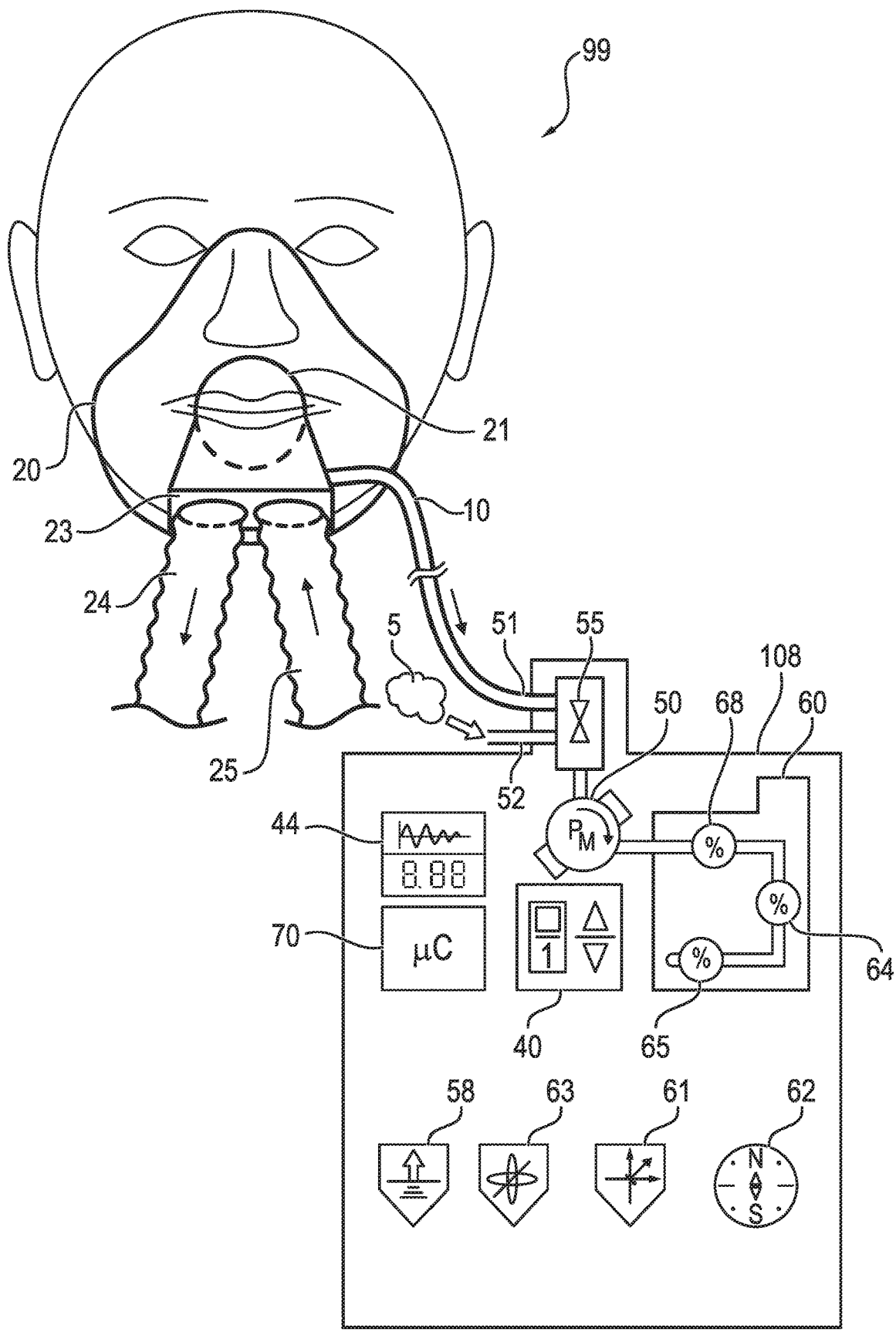
FIG. 4 is a schematic view showing one of two variants of the monitoring systems according to FIGS. 1a, 1b, 2a, 2b, 3 with additional sensor mechanisms.
Figure 5:
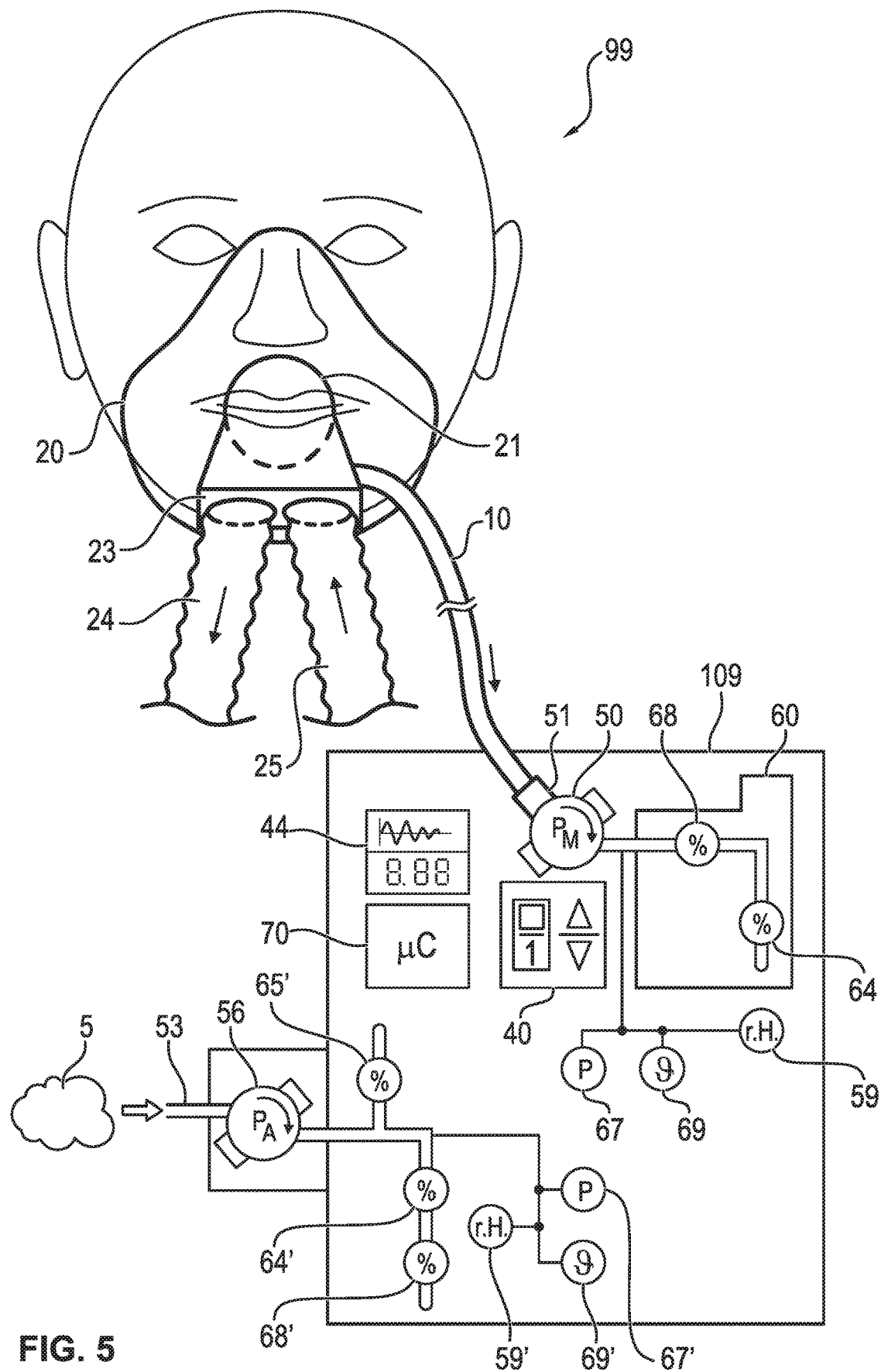
FIG. 5 is a schematic view showing another of two variants of the monitoring systems according to FIGS. 1a, 1b, 2a, 2b, 3 with additional sensor mechanisms.

FIGS. 4 and 5 show variants of the monitoring system 100, 110 according to FIGS. 1a, 1b, 2a, 2b, 3 with additional components of the sensor mechanism 60. The corresponding control lines or signal and data lines for the additional sensors of the sensor mechanism 60 are not shown in FIGS. 4 and 5 for the sake of clarity. Identical elements in FIGS. 1a, 1b, 1c, 2, 3, 4, 5 are designated by the same reference numbers in FIGS. 1a, 1b, 1c, 2, 3, 4, 5. These additional sensors in the sensor mechanism 60 may be used for determining current environmental parameters within and/or outside the cockpit or cabin of the airplane or aircraft and/or for determining current situational parameters and situations as well as for determining physical properties for an additional determination of the composition of the breathing gas. The following additional sensors, which shall also be considered to represent optional possibilities of configuration for FIGS. 1a, 1b, 2a, 2b, 3, 5, shall be shown as examples as additional components of the sensor mechanism 60 in the monitoring system 108 in FIG. 4:

at least one acceleration sensor 61
in the form of a 2-axis or 3-axis acceleration sensor (accelerometer),
at least one compass sensor 62,
for example, an electronic compass,
gyro compass or fluxgate compass,
at least one altitude sensor 58, and
at least one gyro sensor 63.

The following additional sensors, which should also be considered to be optional possibilities of the configuration for FIGS. 1a, 1b, 2a, 2b, 3, 4, are shown as examples in FIG. 5 as additional components of the sensor mechanism 60:

at least one temperature sensor 69, 69',
at least one pressure sensor 67, 67',
at least one humidity sensor 59, 59'.

The additional sensors in the sensor mechanism 60 may be configured as pressure sensors, which may be configured and intended to detect by measurement an ambient pressure from the environment, especially a pressure or a density within and/or outside the cockpit or cabin of the airplane or aircraft and to make it available to the control unit 70. The additional sensors in the sensor mechanism 60 may be configured as temperature sensors, which may be configured and intended to detect by measurement an ambient temperature in the environment, especially a temperature within and/or outside the cockpit or cabin of the airplane or aircraft and to make it available to the control unit 70. These additional sensors in the sensor mechanism 60 may be configured as humidity sensors for detecting an absolute or relative humidity of the environment, which may be configured and intended to detect by measurement a humidity in the environment, especially within and/or outside the cockpit or cabin of the airplane or aircraft and to make it available to the control unit 70. The additional sensors in the sensor mechanism 60 may be configured as at least one additional gas sensor 65 for detecting a gas composition in the environment, which may be configured and intended for detecting by measurement a gas composition in the environment, especially within and/or outside the cockpit or cabin of the airplane or aircraft and to make it available to the control unit 70. Electrochemical gas sensors, catalytic gas sensors, optical, infrared optical gas sensors, photoionization gas sensors, solid electrolyte gas sensors or semiconductor gas sensors may be used as other gas sensors in order to make it possible to also monitor the breathing gas concerning additional substances, such as carbon monoxide, hydrocarbons, residues or products of combustion processes, in addition to the measurement-based detection of concentrations of oxygen and carbon dioxide. A reversing valve 55 shown in FIG. 4, configured, for example, as a valve module or as a part of a valve module, makes possible the switching of quantities or partial quantities of gas samples between the gas inlet 51 and another gas port 52. It is thus made possible to deliver breathing gas from the breathing mask 20 to the sensor mechanism 60 by means of the pump PM 50, on the one hand, but it is also possible, in addition, to deliver quantities of gas or gas mixture from an environment 5 to the sensor mechanism 60 by means of the pump PM and to detect it by measurement by means of the sensor mechanism 60. The reversing valve 55 is controlled by the control unit 70. Outside air can thus be fed from the outside of the airplane or aircraft or inside air can be fed from the cabin or cockpit of the airplane or aircraft via the additional gas port 52 and monitoring of gas concentrations in the breathing mask 20, cockpit, cabin or outside air can alternatingly be made possible, with control by the control unit 70.

The additional sensors 59', 64', 68', 69', which are shown in FIG. 5 in the monitoring system 109 in addition to the other gas sensors 65 and to the sensors 59, 67, 69, are connected pneumatically or fluidically to another pump PA 56. Identical elements in FIGS. 1a, 1b, 1c, 2, 3, 4, 5 are designated by the same reference numbers in FIGS. 1a, 1b, 1c, 2, 3, 4, 5. This additional pump PA 56 makes possible the feed of gas from an environment 5 via an additional gas port 53, for example, of outside air from the outside of the airplane or aircraft or of inside air from the cabin or cockpit of the airplane or aircraft. The additional pump PA 56 is controlled by the control unit 70. Outside air from the outside of the airplane or aircraft or inside air from the cabin or cockpit of the airplane or aircraft can thus be fed via the additional gas port 53. A simultaneous monitoring of gas concentrations in the breathing mask 20 and of gas concentrations in the cockpit, cabin or outside air is thus made possible. Additional sensors in the sensor mechanism 60 may be configured to detect the current situation of the airplane or aircraft by measurement. A current flight situation with flight altitude, flight direction, flight velocity, flight acceleration, flight position with orientation in space (XYZ orientation) and flight situation or flight maneuver (e.g., ascent, descent, curve flight, landing approach, start) can be determined by the control unit (70) by means of the data of an acceleration sensor 61, preferably configured as a 3-axis acceleration sensor (3-axis accelerometer) in combination with an altitude sensor 58 (altimeter), gyro sensor 63 and by the optional addition of information of a compass sensor 62.

Figure 6:
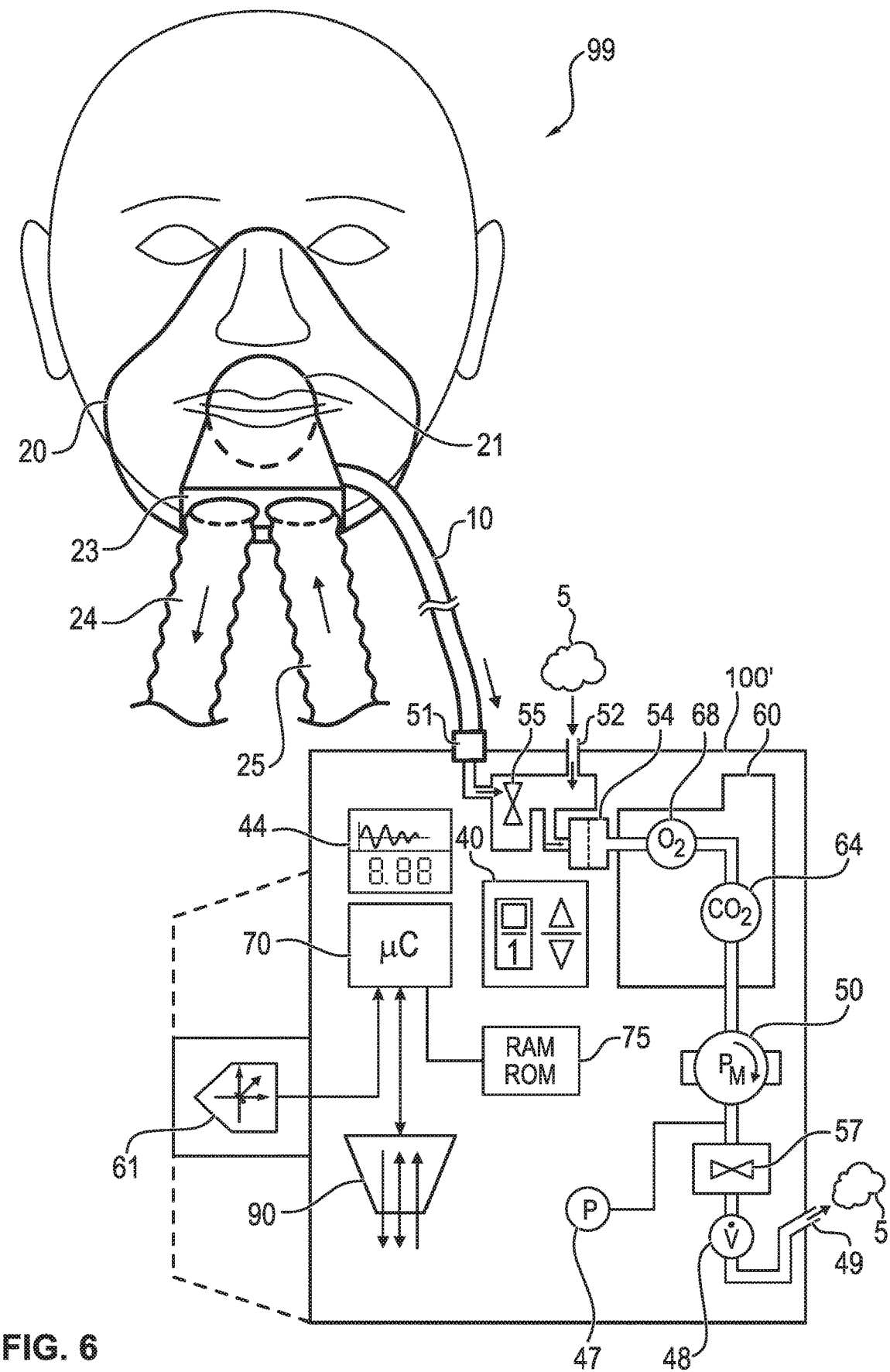
FIG. 6 is a schematic view showing a variant of the monitoring system according to FIG. 3.

FIG. 6 shows a variant as a variant of FIG. 3, wherein the pump PM 50 or the gas transport module is arranged at a gas outlet 49 of the monitoring system 100'. Compared to the variant shown in FIG. 3 with the pump at the gas inlet of the monitoring system, this has the advantage that no traces or impurities can reach the monitoring system 100', especially the sensor mechanism 60 with a carbon dixoide sensor 64 and with an oxygen sensor 68, from the pump PM 50. Identical elements in FIGS. 1a, 1b, 1c, 2, 3, 4, 5, 6 are designated by the same reference numbers in FIGS. 1a, 1b, 1c, 2, 3, 4, 5, 6. Components that may be needed for controlling the pump PM 50 and for the feed of quantities of gases are preferably arranged in the immediate vicinity of the pump PM 50. A pressure sensor 47, a flow sensor 48 and a shut-off valve 57 are arranged for this purpose close to the pump PM 50. The flow sensor 48 is used for a measurement-based control of the flow rate delivered by the pump (PM) 50. After flowing through the pump PM 50 and the flow sensor 48, the quantity of gas being delivered flows to the outside of the monitoring system 100' into the environment 5. The pressure sensor 47 is arranged upstream in the gas stream in relation to the shut-off valve 57 such that the pressure measurement can detect the mask pressure in the breathing mask 20, which pressure is identical now to the pressure level at the gas inlet 51 and to the pressure level in the measured gas line 10 in the closed state of the shut-off valve 57 in the now no-flow state. As an alternative, the pressure sensor may also be arranged at the gas stream in the vicinity of the gas inlet, at the measured gas line 10 or close to the gas sensors 60, 64, 68. A reversing valve 55, which, described in a comparable manner as it was described in connection with the reversing valve 55 in FIG. 4, makes possible a switching of quantities or partial quantities of gas samples between the gas inlet 51 and an additional gas port 52, is provided at the gas inlet 51. The reversing valve is preferably configured as a 3/2-way valve. This arrangement makes it possible to deliver, on the one hand, breathing gas from the breathing mask 20 to the sensor mechanism 60 at the gas inlet 51 by means of the pump PM 50, but it is, moreover, also possible to deliver quantities of gas or gas mixture through the additional gas inlet 52 by means of the pump PM 50 from an environment 5 to the sensor mechanism 60 and to detect it by measurement by means of the sensor mechanism 60. The reversing valve 55 is controlled by the control unit 70. Outside air can thus be fed from the outside of the airplane or aircraft or inside air can be fed from the cabin or cockpit of the aircraft via the additional gas port 52 and—with control by the control unit 70—a monitoring of gas concentrations in the breathing mask 20, cockpit, cabin or outside air can alternatingly be made possible. To protect the sensor mechanism 60 from moisture or condensation, which is fed from the breathing mask 20 through the measured gas line 10 by means of the pump PM 50 to the sensor mechanism 60, a filter element (HME filter) 54 may be arranged in a series connection in the measured gas line or at the outlet of the reversing valve 55.

Instead of the input element 80 configured in the form of a switching element, as in the device 100 according to FIG. 3, an acceleration sensor 61, which is configured and intended as an alternative actuating or input element for detecting actuations performed by the aviator by hand, is provided as an input element in this embodiment 100' according to FIG. 6. By means of this alternative actuating or input element or the acceleration sensor 61, the aviator, pilot or copilot is enabled to mark defined events or situations of the flying operation and also to mark defined personal events, situations or symptoms, for example, those related to health, such as fever, racing heart or a feeling of dizziness in the time course of the mission. This marking may be used by the control unit 70 to combine the events or situations with time information and then to store the combination of time information and event or situation in a memory 75. The memory 75 may be configured as a volatile or non-volatile memory (RAM, ROM, EEPROM) and be arranged either as a fixed component or as a removable memory module (USB stick, SD card) in or at the monitoring system 100'. Provision and/or exchange of the data with an external analysis unit, not shown in the figures, may also be made possible, for example, by means of a data interface 90 in a configuration similar to that shown and described in FIG. 2b. This alternative actuating or input element or the acceleration sensor 61 may thus be used to complement the detected measured values of the sensor mechanism 60 and the events and situations of the flying operation by additional information, which is provided by means of the alternative actuating or input element or of the acceleration sensor 61 by the aviator, pilot or copilot, and to provide it with time information, for example, in the form of a time stamp. It is, however, also possible to configure the alternative actuating or input element or the acceleration sensor 51 as a panic button, which makes it directly possible for the aviator, pilot or copilot to make themself noticeable in a situation that is a special situation according to his perception, for example, a situation with a special, objectively or subjectively perceived danger situation or a risk situation. The marked measured values and/or events, situations as well as the special situations may be made available to the direct external environment, for example, by means of the data interface 90 and may optionally be transmitted, likewise directly (on-line) via a communication system of the airplane or aircraft, to a ground station or to other airplanes or aircraft. Furthermore, an analysis of the marked measured values and/or events, situations and special situations later after the mission (off-line) is made possible by means of the memory 75 or of the data interface 90.

Figure 7:
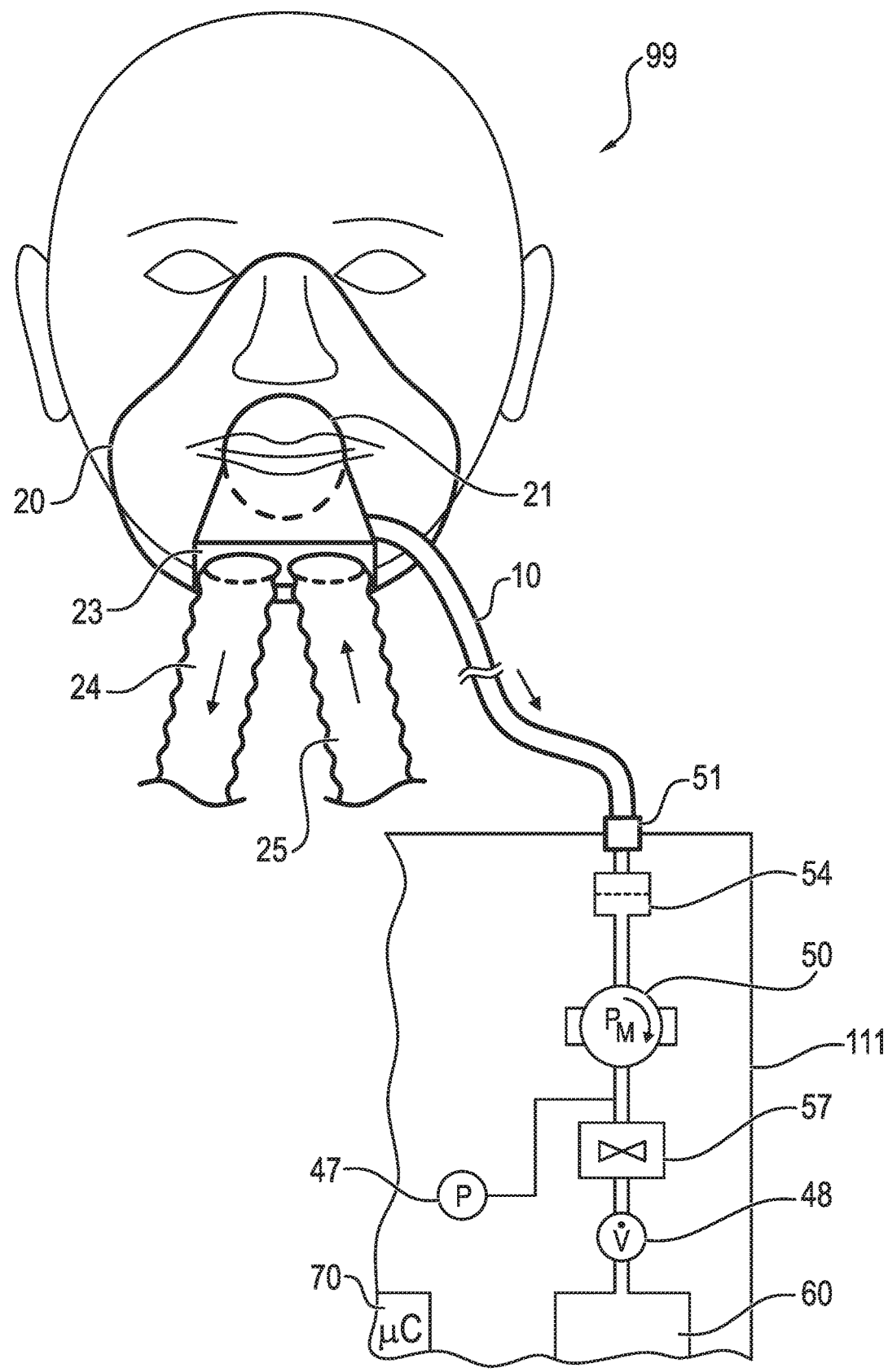
FIG. 7 is a schematic view showing another variant of the monitoring system according to FIG. 3.

FIG. 7 shows, in a detail view as a detail drawing of the area around the gas inlet 51 and unlike the view in FIG. 6, a monitoring system 111 with an arrangement of filter element (HME filter) 54, pump PM 50, sensor mechanism 60, pressure sensor 47, flow sensor 48, shut-off valve 57 in an arrangement at the gas inlet 51 without reversing valve for switching between a monitoring of breathing gases of the pilot and a monitoring of the cabin air. Identical elements in FIGS. 1a, 1b, 1c, 2, 3, 4, 5, 6, 7 are designated by the same reference numbers in FIGS. 1a, 1b, 1c, 2, 3, 4, 5, 6, 7. The pressure sensor 47 is arranged upstream, in the gas stream in relation to the shut-off valve 57 such that the flow measurement can detect in the now no-flow state the mask pressure in the breathing mask 20, which is now identical to the pressure level at the gas inlet 51 and in the measured gas line 10. As an alternative, the pressure sensor 47 may also be arranged at the gas stream in the vicinity of the gas inlet 51, at the measured gas line 10 or close to the sensor mechanism 60 with the gas sensors.

Figure 8:
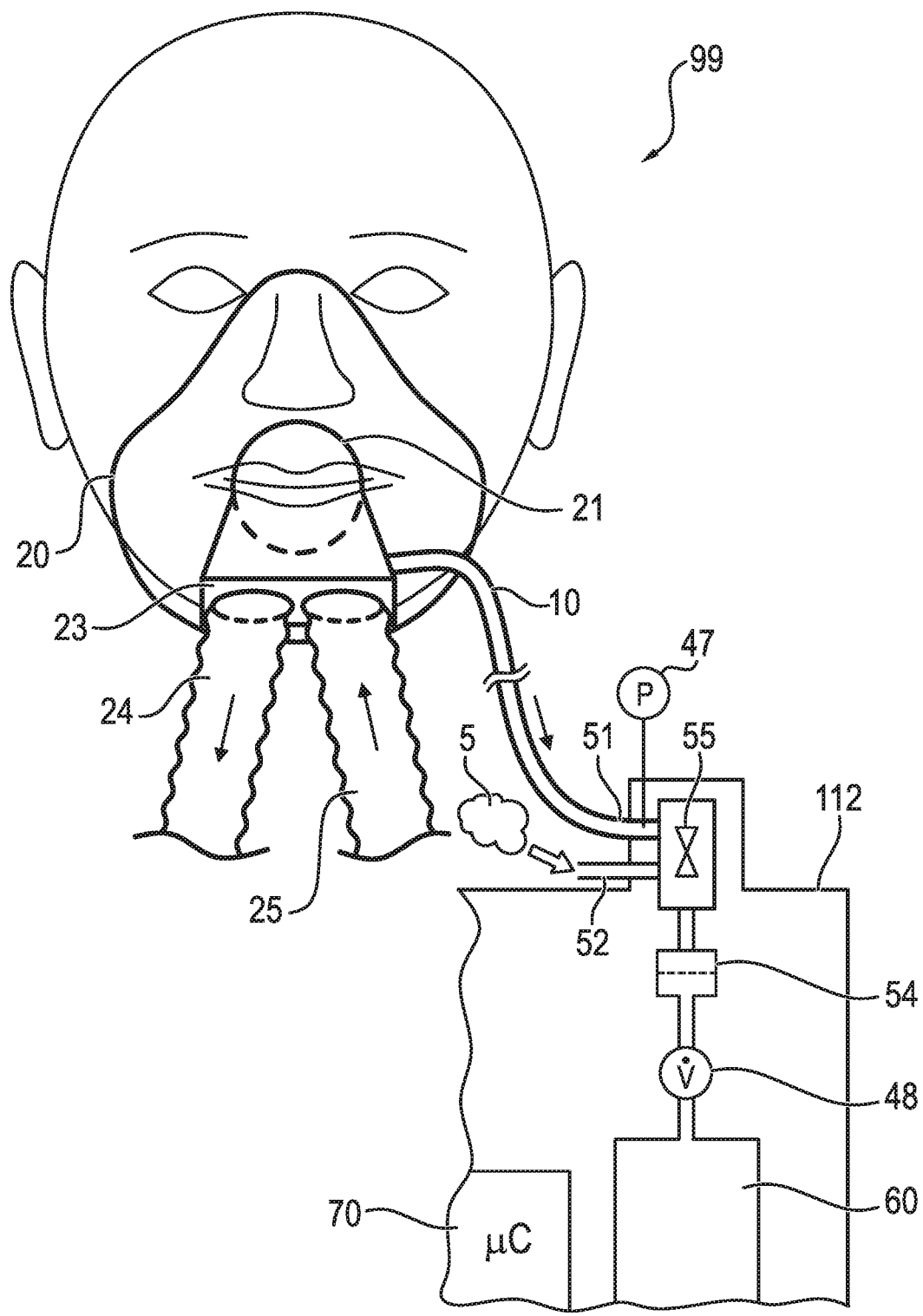
FIG. 8 is a schematic view showing an alternative variant of the monitoring system according to FIG. 6.

FIG. 8 shows, as a detail view as a detail drawing of the area around the gas inlet 51 and unlike the view in FIGS. 6 and 7, a monitoring system 111, 112 with an arrangement of filter element (HME filter) 54, pump PM 50, sensor mechanism 60, pressure sensor 47 at the gas inlet 51 and with a reversing valve 55 configured as a 3/2-way valve. Identical elements in FIGS. 1*a*, 1*b*, 1*c*, 2, 3, 4, 5, 6, 7, 8 are designated by the same reference numbers in FIGS. 1*a*, 1*b*, 1*c*, 2, 3, 4, 5, 6, 7, 8. The reversing valve 55 can release the path for quantities of gas from an environment 5, e.g., the cabin, to the sensor mechanism 60 and thus make a cabin air monitoring possible. The reversing valve closes at the same time the path for quantities of gas from the breathing mask 20. The reversing valve 55 also has in this configuration according to FIG. 8 a manner of functioning as a shut-off valve for the performance of a measurement maneuver for determining the pressure in the breathing mask in addition to the switching between the measurement of breathing gases and cabin air. The pressure sensor 47 is arranged at the gas inlet 51 in relation to the reversing valve 55 and the measured gas line 10 such that in the state of the reversing valve 55 with cabin air monitoring, the pressure measurement can detect the mask pressure in the breathing mask 20, which is now identical to the pressure level at the gas inlet 51 and in the measured gas line 10. The reversing valve 55 makes it possible to switch between monitoring of breathing gases of the pilot and monitoring of the cabin air.

Figure 9:
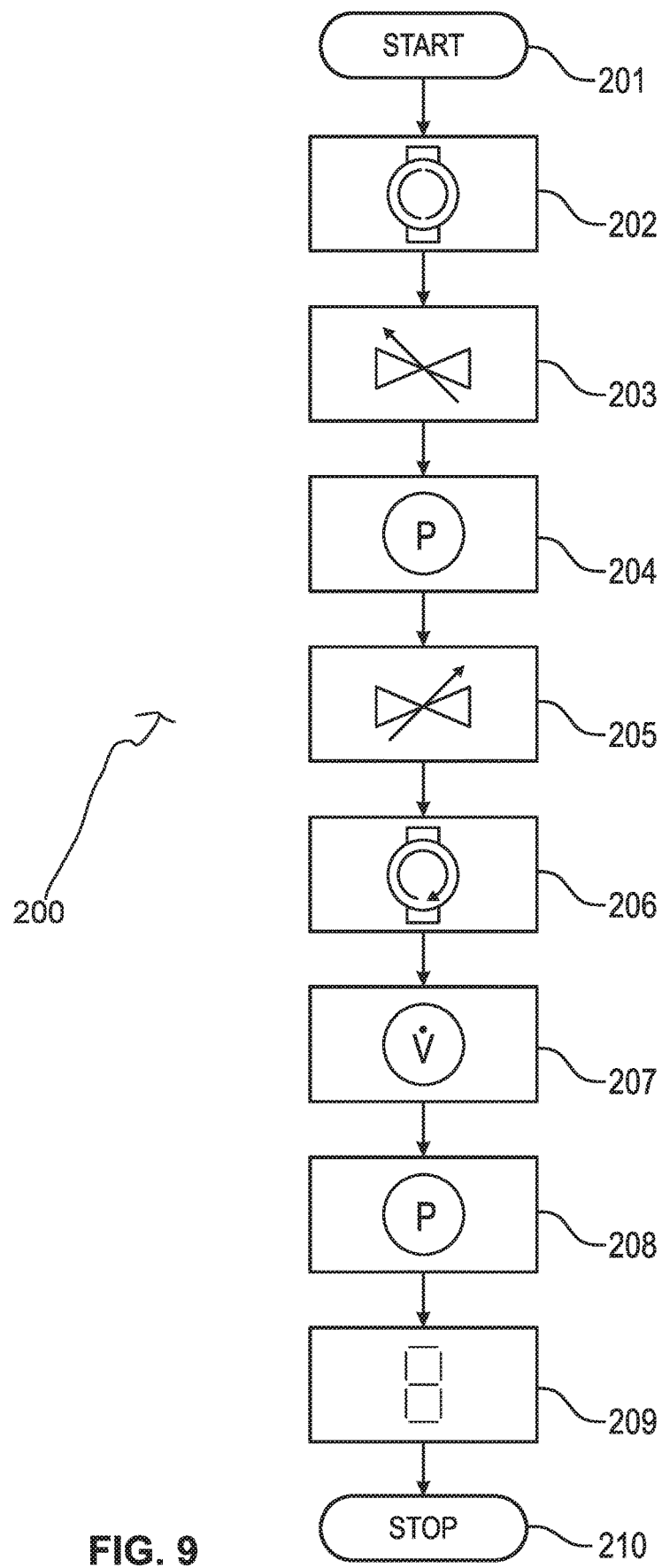
FIG. 9 is a schematic view showing a flow chart for determining a pressure in a breathing mask.

FIG. 9 schematically shows a procedure 200 of a measurement maneuver for determining a pressure level in the breathing mask 20 (FIG. 6) with a monitoring system 100' according to FIG. 6. Identical elements in FIGS. 1*a*, 1*b*, 1*c*, 2, 3, 4, 5, 6, 7, 8, 9 are designated by the same reference numbers in FIGS. 1*a*, 1*b*, 1*c*, 2, 3, 4, 5, 6, 7, 8, 9. Beginning with a start 201, the measurement maneuver is carried out in an embodiment with a shut-off valve (flow-lock valve) 57 (FIG. 6) by the control unit 70 (FIG. 6). A deactivation 202 of the pump PM 50 (FIG. 6) is carried out after the START 201, and the shut-off valve 57 (FIG. 6) is closed at that time or with a slight time delay. The flow is thus stopped in the measured gas line 10 (FIG. 6) and the sensor mechanism 60 (FIG. 6) comes into a resting state. A first measurement operation of a pressure measurement 204 is carried out to determine the static pressure level. The shut-off valve 57 (FIG. 6) is then opened 205 and the pump PM 50 (FIG. 6) is activated 206. The pump PM 50 (FIG. 6) begins to suck quantities of gas from the breathing mask 20 (FIG. 6) through the measured gas line 10 (FIG. 6) and the sensor mechanism 60 (FIG. 6) at a defined flow rate in the range of 50 mL/min to 100 mL/min A flow measurement 207 is carried out now with the flow sensor 48 (FIG. 6) to control and monitor the flow rate. An additional measurement operation of a pressure measurement 208 is subsequently carried out to determine the dynamic pressure level. A difference value, which indicates the current pressure drop over the pneumatic system, is determined 209 from the pressure measured values of the first pressure measurement 204 and the additional pressure measurement 208. The measurement maneuver procedure thus comes to an end 210. The difference value thus determined can then be made available and used to determine the mask pressure during the further operation of the monitoring system during the mission of the aircraft.

While specific embodiments of the invention have been shown and described in detail to illustrate the application of the principles of the invention, it will be understood that the invention may be embodied otherwise without departing from such principles.

LIST OF REFERENCE NUMBERS

5 Environment, atmosphere, outside air, cockpit or cabin
10 Measured gas line
20 Breathing mask
21 Gas port at the breathing mask
24, 25 Hose lines
23, 23' Connection element
29 Exhalation valve
40 Operating elements
44, 45 Display elements
46 Wireless interface, radio interface
47 Pressure sensor
48 Flow sensor (flow sensor, delta P sensor)
49 Gas outlet
50 Gas delivery module, pump PM
51 Gas inlet
52, 53 Additional gas port
54 Filter element (HME filter)
55 Reversing valve (3/2-way valve), valve module
56 Additional pump PA
57 Shut-off valve (flow lock valve)
58 Altitude sensor (altimeter)
59, 59'Humidity sensor
60 Sensor mechanism
61 Acceleration sensor
62 Compass sensor
63 Gyro sensor
64, 64'Carbon dioxide sensor
65 Additional gas sensor
66 Sensor
67, 67'Pressure sensor
68, 68'Oxygen sensor
69, 69 Temperature sensor
70 Control unit
80 Input element
90 Data interface
99 Person, pilot, aviator
100, 100'Monitoring system
108,109,110,111,112 Monitoring system
200 Measurement maneuver procedure
201 Beginning, START
202 Pump: Deactivation
203 Shut-off valve: Close valve
204 First pressure measurement: Static pressure level
205 Shut-off valve: Open valve
206 Pump: Activation
207 Flow measurement
208 Additional pressure measurement: Dynamic pressure level
209 Determination of the value of the current pressure drop
210 End, STOP

What is claimed is:

1. A monitoring system for monitoring a gas composition of air, breathing air or breathing gases in airplanes or aircraft, the monitoring system comprising:
a monitoring system mobile module configured as a construction that is to be arranged in or at clothing of an aviator, pilot, copilot or aircrew and/or to be worn, carried, or attached to the aviator, pilot, copilot or aircrew;

a sensor mechanism carried by the mobile module and configured as a paramagnetic oxygen sensor configured to provide a qualitative and quantitative measurement-based detection of oxygen based on paramagnetic properties of oxygen, wherein the sensor mechanism further comprises a sensor configured as a carbon dioxide sensor;

a control unit carried by the mobile module and configured to organize a procedure of a measurement-based monitoring of the gas composition of air, breathing air or breathing gases with the sensor mechanism in an airplane or aircraft, and to control or regulate the procedure of the measurement-based monitoring of the gas composition of air, breathing air or breathing gases in the airplane or aircraft, wherein the procedure of the measurement-based monitoring comprises a qualitative and quantitative measurement-based detection of a concentration of oxygen with the paramagnetic oxygen sensor, wherein the procedure of the measurement-based monitoring further comprises a qualitative and quantitative measurement-based detection of a concentration of carbon dioxide with the sensor mechanism; and a gas transport module carried by the mobile module and comprising a pump, configured as a piezoelectrically driven pump, with a gas port for connection with a measured gas line to deliver quantities or partial quantities of breathing gas or breathing air from a measuring point, via the measured gas line, to the sensor mechanism.

2. A monitoring system in accordance with claim 1, wherein the sensor mechanism is configured with a carbon monoxide sensor and the procedure of the measurement-based monitoring further comprises a qualitative and quantitative measurement-based detection of a concentration of carbon monoxide with the sensor mechanism.

3. A monitoring system in accordance with claim 1, wherein the control unit is configured to also take into consideration and/or to also include in the procedure at least one environmental parameter and/or at least one situational parameter.

4. A monitoring system in accordance with claim 1, further comprising a data interface carried by or connected directly to the mobile module.

5. A monitoring system in accordance with claim 1, further comprising a data interface carried by or connected directly to the mobile module and configured to receive and/or provide environmental parameters and/or situational parameters.

6. A monitoring system in accordance with claim 1, wherein the sensor mechanism comprises:

a sensor configured as a gas sensor; and an additional sensor carried by or connected directly to the mobile module and configured to determine and/or to measurement-based detect environmental parameters and/or to determine and/or to measurement-based detect situational parameters and wherein the sensor mechanism is configured for providing the environmental parameters and/or situational parameters.

7. A monitoring system in accordance with claim 1, further comprising a gas inlet of the monitoring system carried by the mobile module, wherein the gas transport module is arranged at or adjacent to the gas inlet of the monitoring system.

8. A monitoring system in accordance with claim 1, further comprising a gas outlet of the monitoring system carried by the mobile module, wherein the gas transport module is arranged at or adjacent to the gas outlet of the monitoring system.

9. A monitoring system in accordance with claim 1 further comprising: an additional gas port; and a reversing valve carried by the mobile module.

10. A monitoring system in accordance with claim 9, further comprising an additional pump arranged at the additional gas port.

11. A monitoring system in accordance with claim 1, wherein the control unit is configured to control the gas transport module.

12. A monitoring system in accordance with claim 11, wherein the sensor mechanism comprises:

a sensor configured as a gas sensor; and an additional sensor carried by or connected directly to the mobile module and configured to determine and/or to measurement-based detect environmental parameters and/or to determine and/or to measurement-based detect situational parameters and wherein the sensor mechanism is configured for providing the environmental parameters and/or situational parameters, wherein the control unit is configured to also take into consideration and/or to also include in the control at least one environmental parameter and/or at least one situational parameter.

13. A monitoring system in accordance with claim 1, wherein the control unit is configured to determine and/or detect an alarm situation and to organize an alarm generation or alarm and/or provide an alarm signal.

14. A monitoring system in accordance with claim 13, wherein the control unit is configured to also take into consideration an environmental parameter and/or a situational parameter in the organization of the alarm generation or alarm and/or to also include the environmental parameter and/or the situational parameter in the organization of the alarm generation.

15. A monitoring system in accordance with claim 1, further comprising at least one an energy storage device carried by or connected directly to the mobile module.

16. A monitoring system in accordance with claim 1, further comprising at least one operating element, for operating the monitoring system, the operating element being carried the mobile module.

17. A monitoring system in accordance with claim 1, further comprising at least one display element for displaying events, situations, status data, current measured values, past measured values, measured variables derived from measured values, including maxima or minima, mean values, trends, statistics, events and alarm situations, the display element being carried the mobile module.

18. A monitoring system in accordance with claim 1, further comprising an input element configured to receive user input comprising user initiates annotation, triggering, starting or ending defined situations, defined actions or states at the monitoring system, the input element being carried the mobile module.

19. A monitoring system in accordance with claim 18, wherein the input element is configured as an acceleration sensor carried the mobile module.

20. A monitoring system in accordance with claim 1, further comprising a memory for storing measured values and measured variables derived from the measured values including maxima or minima, mean values, trends, statistics, events, alarm situations, the memory being carried the mobile module.

21. A monitoring system in accordance with claim 3, wherein the control unit is configured to also take into consideration an environmental parameter and/or a situational parameter during signal processing and/or signal filtering of the measured values of the sensor mechanism and/or to also include the environmental parameter and/or the situational parameter in an adaptation of the signal processing.

22. A monitoring system in accordance with claim 1, further comprising a monitoring system memory, wherein the control unit is configured to use predefined threshold values, which are storable for determined values of gas concentrations in the monitoring system memory, in the organization of the alarm generation.

23. A monitoring system in accordance with claim 1, wherein the control unit is configured to use an early warning system for the detection of hypoxia on a basis of current and past measured values of the sensor mechanism by means of a decision matrix or adapted algorithms or teachable or self-learning algorithms.

24. A monitoring system in accordance with claim 23, wherein the control unit is configured to take into consideration physiological data in the early warning system for the detection of hypoxia.

25. A monitoring system in accordance with claim 1, wherein an HME filter element is arranged in the measured gas line, at the gas inlet or at the gas transport module.

26. A monitoring system in accordance with claim 1 in combination with a breathing gas mask connected to the sensor mechanism by a measured gas line and further comprising:
a memory;
a pressure sensor; and
a shut-off valve, wherein the control unit is configured together with a pressure sensor and the shut-off valve and the memory to determine a current pressure level in the breathing mask.

27. A monitoring system in accordance with claim 26, wherein the control unit is configured
to determine a static pressure level and a dynamic pressure level;
to determine an offset pressure level based on a static pressure level and a dynamic pressure level; and
determine the current pressure level in the breathing mask taking into consideration the dynamic pressure level by means of a measurement maneuver.

28. A monitoring system in accordance with claim 27, wherein the control unit is configured to take into consideration information concerning breathing phases of an aviator user of the breathing mask during the measurement-based detection and/or determination of the static pressure measured value and/or of the dynamic pressure measured value during the performance of the measurement maneuver.

29. A process for operating a monitoring system, the process comprising the steps of:
providing a monitoring system for monitoring a gas composition of air, breathing air or breathing gases in airplanes or aircraft, the monitoring system comprising a mobile module configured as a construction that is to be arranged in or at clothing of an aviator, pilot or copilot and/or to be worn, carried, or attached to the pilot, a sensor mechanism carried by the mobile module, wherein the sensor mechanism comprises an oxygen sensor configured as a paramagnetic oxygen sensor to detect a concentration of oxygen based on paramagnetic properties of oxygen, wherein the sensor mechanism further comprises a sensor configured as at least one of a carbon dioxide sensor and a carbon monoxide sensor, and a control unit control unit carried by the mobile module and configured to organize a procedure of a measurement-based monitoring of the gas composition of air, breathing air or breathing gases with the sensor mechanism in an airplane or aircraft, and to control or regulate the procedure of the measurement-based monitoring of the gas composition of air, breathing air or breathing gases in the airplane or aircraft, wherein the procedure of the measurement-based monitoring comprises a qualitative and quantitative measurement-based detection of a concentration of oxygen with the paramagnetic oxygen sensor, wherein the procedure of the measurement-based monitoring further comprises a qualitative and quantitative measurement-based detection of a concentration of carbon dioxide with the sensor mechanism, a gas transport module carried by the mobile module and comprising a pump, configured as a piezoelectrically driven pump, with a gas port for connection with a measured gas line to deliver quantities or partial quantities of breathing gas or breathing air from a measuring point, via the measured gas line, to the sensor mechanism, and a gas outlet carried by the mobile module of the monitoring system, wherein the gas transport module is arranged at or adjacent to the gas outlet of the monitoring system;
activating the sensor mechanism of the monitoring system;
preparing a data storage with initialization of a memory of the monitoring system;
carrying out a qualitative and quantitative measurement-based detection of measured values of the paramagnetic oxygen sensor to detect the concentration of oxygen in the air, breathing air or breathing gases; and
storing data of the measured values, as a data storage of the measured values of the sensor mechanism, in the memory with corresponding time information by the control unit.

30. A process in accordance with claim 29, wherein an additional storage of situational parameters and/or environmental parameters is carried out with the corresponding time information during the data storage of the measured values of the sensor mechanism.

31. A process for operating a monitoring system in accordance with claim 29, further comprising providing an input element carried by the mobile module and configured to receive user input comprising user initiated annotation, triggering, starting or ending defined situations, defined actions or states at the monitoring system, wherein an additional detection of measured values of the sensor mechanism, which detection is independent from a time control, is carried out in case of activation of the input element on activation of an input element.

32. A monitoring system for monitoring a gas composition of air, breathing air or breathing gases in airplanes or aircraft, the monitoring system comprising:
a measured gas line in fluid connection with a measuring point of a breathing gas mask, with the gas composition of air, breathing air or breathing gases;
a mobile module configured as a construction that is to be arranged in or at clothing of an aviator, pilot or copilot and/or to be worn, carried, or attached to the pilot;
a sensor mechanism configured as a part of the mobile module and comprising a paramagnetic oxygen sensor and a carbon dioxide sensor configured as an IR sensor, configured to provide a qualitative and quantitative measurement-based detection of oxygen based on paramagnetic properties of oxygen, wherein the sensor mechanism further comprises a sensor configured as at least one of a carbon dioxide sensor and a carbon monoxide sensor;
- a gas transport module configured as a part of the mobile module and comprising a pump, configured as a piezoelectrically driven pump, with a gas port connected with the measured gas line to deliver quantities or partial quantities of the air, breathing air or breathing gases from the measuring point, via a measured gas line, to the sensor mechanism;
- a gas outlet of the monitoring system configured as a part of the mobile module and, wherein the gas transport module is arranged at or adjacent to the gas outlet of the monitoring system; and
- a control unit configured as a part of the mobile module and configured to organize a procedure of a measurement-based monitoring of the gas composition of air, breathing air or breathing gases with the sensor mechanism in the airplane or aircraft, to control the gas transport module and to control or regulate the procedure of the measurement-based monitoring of the gas composition of air, breathing air or breathing gases in the airplane or aircraft, wherein the procedure of the measurement-based monitoring comprises a qualitative and quantitative measurement-based detection of a concentration of oxygen with the sensor mechanism, and comprises a qualitative and quantitative measurement-based detection of a concentration of carbon dioxide with the sensor mechanism.

33. A process in accordance with claim 29, further providing an HME filter element which is arranged in the measured gas line, at a gas inlet or at the gas transport module.

34. A monitoring system for monitoring a gas composition of air of claim 33, wherein an HME filter element is arranged in the measured gas line, at the gas inlet or at the gas transport module.

35. A monitoring system in accordance with claim 32, further comprising an input element configured as a part of the mobile module and configured to receive user input comprising user initiates annotation, triggering, starting or ending defined situations, defined actions or states at the monitoring system, wherein the input element is configured as an acceleration sensor that also detects airplanes or aircraft situational parameters and data.

36. A monitoring system in accordance with claim 32, further comprising at least one an energy storage device configured as a part of the mobile module.

* * * * *